United States Patent [19]
Marnett et al.

[11] Patent Number: 5,973,191
[45] Date of Patent: Oct. 26, 1999

[54] SELECTIVE INHIBITORS OF PROSTAGLANDIN ENDOPEROXIDE SYNTHASE-2

[75] Inventors: Lawrence J. Marnett; Amit S. Kalgutkar, both of Nashville, Tenn.

[73] Assignee: Vanderbilt University, Nashville, Tenn.

[21] Appl. No.: 08/774,542

[22] Filed: Dec. 30, 1996

[51] Int. Cl.$^6$ .................... C07C 69/78; A61K 31/235
[52] U.S. Cl. .................... 560/142; 560/145; 560/226; 560/227; 514/544
[58] Field of Search ................. 560/142, 145, 560/226, 227; 514/544

[56] References Cited

PUBLICATIONS

McKinnon, Acyl transfer in o–hydroxybenzenethiol, Can. J. Chem., vol. 58, pp. 2761–2764, Dec. 1980.
Bonsignore et al., Studies on the . . . –Acetic Anhydride, J. Heterocyclic Chem., vol. 21, pp. 573–576, Mar. 1984.
Poirier et al., Preparation of phenolic sulfides . . . , Sulfur Letters, vol. 10(3–4), pp. 169–173, Sep. 1989.
Arnoldi et al., Isovanillyl sweetners . . . , J. Chem. Soc., Perkin Trans. 1, vol. 12, pp. 1359–1366, Jun. 1993.

*Primary Examiner*—Samuel Barts
*Assistant Examiner*—Rosalynd Keys
*Attorney, Agent, or Firm*—Benjamin Aaron Adler

[57] ABSTRACT

The present invention provides a compound of the formula (I)

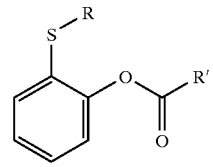

wherein R is selected from the group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_2O(CH_2)_3CH_3$, $CH_2HC=CH(CH_2)_3CH_3$, $CH_2C\equiv C(CH_2)_3CH_3$, $CH_2C\equiv C(CH_2)_2CH_3$, $CH_2C\equiv CCH_2CH_3$, $CH_2C\equiv CCH_3$ and $CH_2C\equiv CH$; and R' is selected from the group consisting of $CH_3$, $CF_3$, $CH_2Cl$ and $CH_2Br$ or a pharmaceutically acceptable salt or hydrate thereof. Also provided is a method of inhibiting the synthesis of prostaglandin endoperoxide syntase-2 (PGHS-2) in a mammal.

22 Claims, 26 Drawing Sheets

2-acyloxythioanisoles 6-14
(see Table 1)

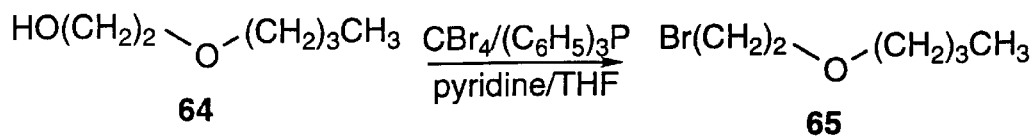
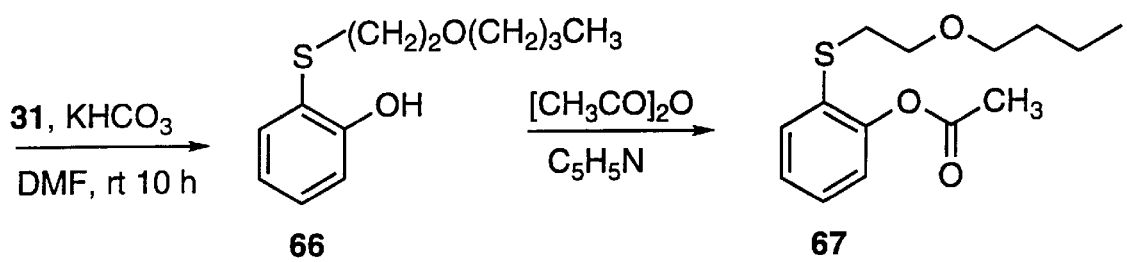
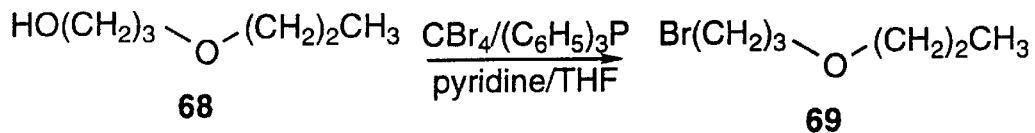
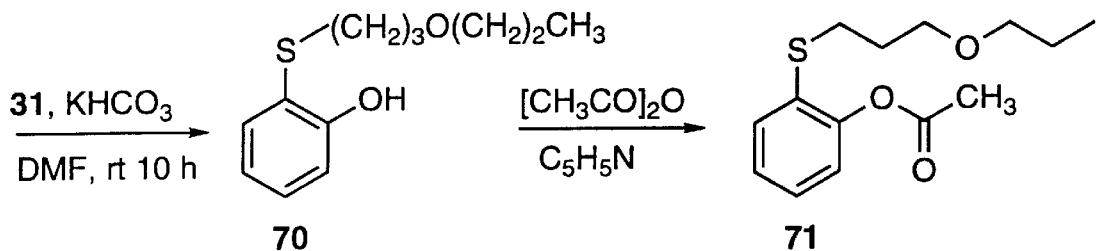
FIG. 2G

SELECTIVE INHIBITORS OF PROSTAGLANDIN ENDOPEROXIDE SYNTHASE-2

FEDERAL FUNDING LEGEND

This invention was produced in part using funds obtained through grant CA47479 from the National Institutes of Health. Consequently, the government has certain rights in this invention.

BACKGROUND OF THE INVENTION

1. Field of the Invention

The present invention relates generally to the fields of molecular pharmacology and the biochemistry of inflammation. More specifically, the present invention relates to a selective 2-acyloxyphenylalkyl and 2-acyloxyphenylaryl sulfide inhibitors of prostaglandin endoperoxide synthase-2.

2. Description of the Related Art

Prostaglandins, particularly prostaglandin $E_2$ ($PGE_2$), are involved in many diverse physiological and pathophysiological functions. These eicosanoids are produced by the action of prostaglandin endoperoxide synthase (PGHS, EC 1.14.99.1) on arachidonic acid. Prostaglandin endoperoxide synthase activity originates from two distinct and independently regulated isozymes, termed as prostaglandin endoperoxide synthase-1 and prostaglandin endoperoxide synthase-2 and are encoded by two different genes (1,2).

Prostaglandin endoperoxide synthase-1 is expressed constitutively and is thought to play a physiological role, particularly in platelet aggregation, cytoprotection in the stomach, and regulation of normal kidney function (FIG. 1). Prostaglandin endoperoxide synthase-2 is the inducible isozyme and expression of prostaglandin endoperoxide synthase-2 is induced by a variety of agents which include endotoxin, cytokines, and mitogens (2,3). Importantly, prostaglandin endoperoxide synthase-2 is induced in vivo in significant levels upon pro-inflammatory stimuli (4).

These discoveries led to the proposal that prostaglandin endoperoxide synthase-1 and prostaglandin endoperoxide synthase-2 serve different physiological and pathophysiological functions. For example, the disruption of beneficial prostaglandin production by all of the currently used non-steroidal antiinflammatory drugs (NSAIDs) results in a mechanism-based toxicity mainly in the gastrointestinal tract and kidney and thus limits their therapeutic usefulness especially when long-term treatment is involved (5–7). As a result of this critical finding, a major discovery effort has been excecuted in the pharmaceutical industry to identify selective and orally active prostaglandin endoperoxide synthase-2 inhibitors because they may provide the desired anti-inflammatory and analgesic properties without the deleterious and sometimes life threatening side effects commonly associated with the existing non-steroidal antiinflammatory drugs.

The prior art is deficient in the lack of selective and orally active prostaglandin endoperoxide synthase-2 inhibitors. The present invention fulfills this longstanding need and desire in the art.

SUMMARY OF THE INVENTION

In one embodiment of the present invention, there is provided a compound of the formula

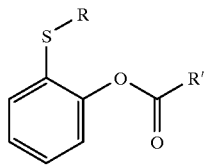

(I)

wherein R is selected from the group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_2O(CH_2)_3CH_3$, $CH_2HC=CH(CH_2)_3CH_3$, $CH_2C\equiv C(CH_2)_3CH_3$, $CCH_2C\equiv C(CH_2)_2CH_3$, $CH_2C\equiv C-CCH_2CH_3$, $CH_2C\equiv C-CH_3$ and $CH_2C\equiv CH$; and R' is selected from the group consisting of $CH_3$, $CF_3$, $CH_2Cl$ and $CH_2Br$ or a pharmaceutically acceptable salt or hydrate thereof.

In another embodiment of the present invention, there is provided a pharmaceutical composition, comprising the novel compounds of the present invention and a pharmaceutically acceptable carrier.

In yet another embodiment of the present invention, there is provided a method of inhibiting the synthesis of prostaglandin endoperoxide syntase-2 (PGHS-2) in a mammal in need of such treatment, comprising the step of administering to said mammal an effective amount of a compound of Formula (I).

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2G shows the synthetic scheme for the synthesis of compounds 65, 66, 67, 69, 70 and 71. FIG. 2I shows the synthetic scheme for the synthesis of compounds 79–91.

DETAILED DESCRIPTION OF THE INVENTION

Figure 1:
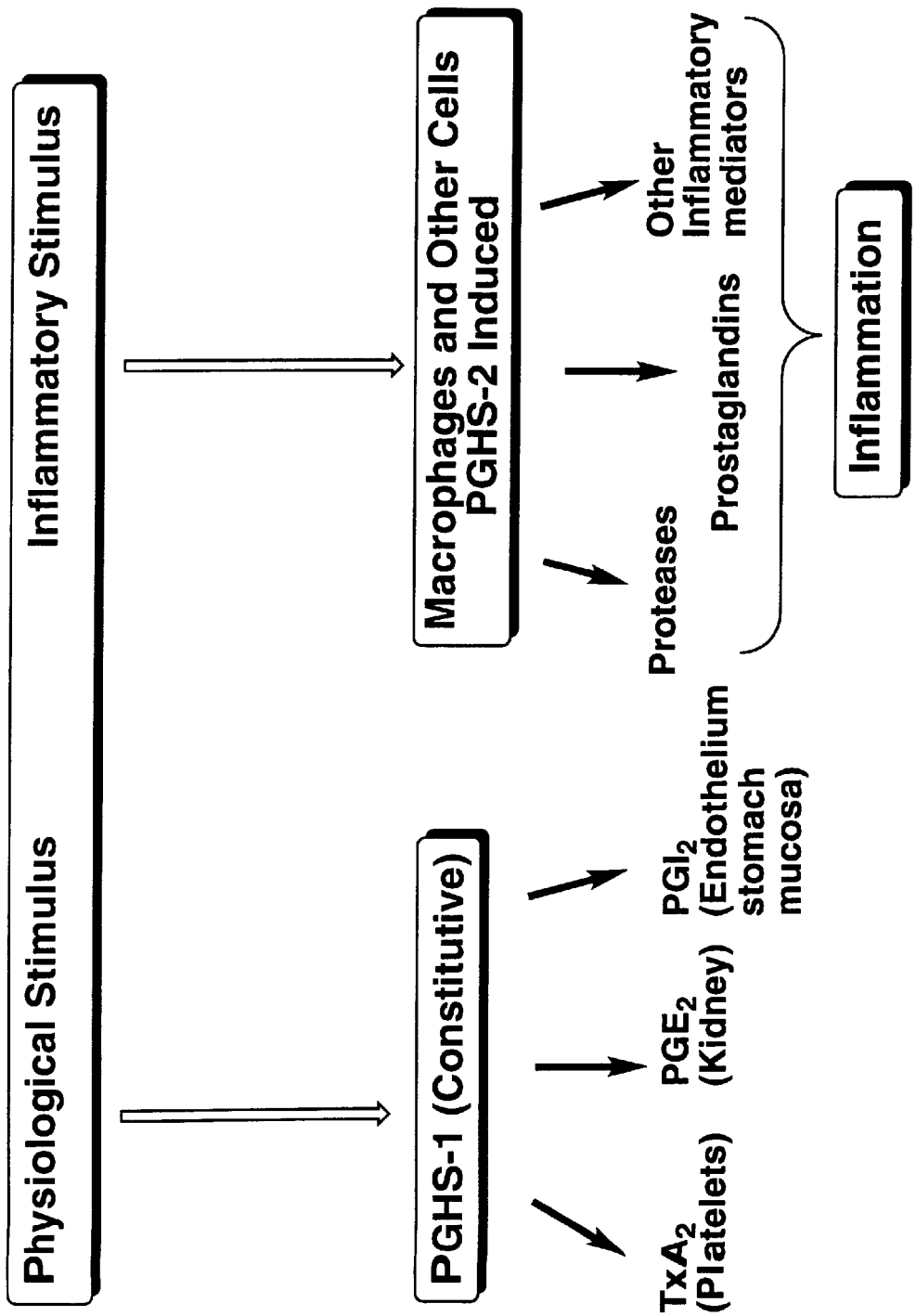
FIG. 1 shows a schematic of the physiological stimuli which lead to inflammation.

Two general structural classes of prostaglandin endoperoxide synthase-2 selective inhibitors are commonly reported in the literature. In addition to selective prostaglandin endoperoxide synthase-2 inhibition in vitro, many of these compounds possess potent anti-inflammatory activity in the rat adjuvant-induced arthritis model along with exceptional safety profiles in comparison with the existing antiinflammatory agents. The structural classes include the tricyclic non-acidic arylmethyl sulfones (8–11) (exemplified by DuP 697 and SC 8092) and the acidic sulfonamides (12–15) (exemplified by Flosulide and NS-398) (FIG. 2). The arylmethyl sulfonyl moiety in the tricyclic non-acidic compounds such as SC 8092 is thought to play a key role in the selective prostaglandin endoperoxide synthase-2 inhibition by these compounds as reduction of the sulfone group in SC 8092 to the corresponding sulfide functionality generates SC 8076, a prostaglandin endoperoxide synthase-1 selective inhibitor (11) (see FIG. 2).

In the present invention, a variety of substituted acyloxybenzene derivatives were synthesized and examined as selective prostaglandin endoperoxide synthase-2 inhibitors. Introduction of a 2-methylthio functionality leads to the corresponding 2-acetoxythioanisole 2 derivative which displays selective inhibition of the cyclooxygenase activity of prostaglandin endoperoxide synthase-2 ($IC_{50}$ (PGHS-2) ~264 $\mu$M; $IC_{50}$ (PGHS-1)>5 mM).

Attempts to improve the potency of 2 as a prostaglandin endoperoxide synthase-2 selective inhibitor has led to the discovery of novel 2-acetoxyphenyl alkyl and aryl sulfides some of which are ~300 times more potent than 2 as prostaglandin endoperoxide synthase-2 selective inhibitors. Thus, the present invention provides the discovery of a new structural class of selective prostaglandin endoperoxide synthase inhibitors. Subsequent inhibition studies with $^{14}$C-radiolabled inhibitors have established that selective prostaglandin endoperoxide synthase-2 inhibition arises from acetylation of an active site amino acid residue. The present invention is the first documentation of a selective covalent modification of prostaglandin endoperoxide synthase-2 by a selective prostaglandin endoperoxide synthase-2 inhibitor. In addition to the in vitro inhibition studies with purified human prostaglandin endoperoxide synthase-2 and ovine prostaglandin endoperoxide synthase-1, the ability of these new compounds in inhibiting prostaglandin endoperoxide synthase-2 activity in murine macrophages was also examined. Most of the inhibitors displayed potent inhibition of the prostaglandin endoperoxide synthase-2 activity in murine macrophages activated with LPS and IFN-$\gamma$ indicating that these compounds are active in vivo as well.

The present invention is directed to a compound of the formula

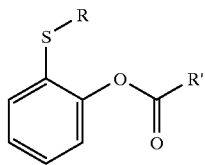

(I)

wherein R is selected from the group consisting of $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $(CH_2)_2O(CH_2)_3CH_3$, $CH_2HC{=}CH(CH_2)_3CH_3$, $CH_2C{\equiv}C(CH_2)_3CH_3$, $CH_2C{\equiv}C(CH_2)_2CH_3$, $CH_2C{\equiv}C{-}CH_2CH_3$, $CH_2C{\equiv}CCH_3$ and $CH_2C{\equiv}CH$; and R' is selected from the group consisting of $CH_3$, $CF_3$, $CH_2Cl$ and $CH_2Br$ or a pharmaceutically acceptable salt or hydrate thereof. Preferably, the representative examples of compounds of the present invention are selected from the group consisting of 2-acetoxythioanisole, 2-(trifluoromethylacetoxy)thioanisole, 2-($\alpha$-chloroacetoxy)thioanisole, 2-($\alpha$-bromoacetoxy)thioanisole, 2-acetoxyphenylbenzyl sulfide, 2-acetoxyphenyl-2-phenylethyl sulfide, 2-acetoxyphenylethyl sulfide, 2-acetoxyphenylpropyl sulfide, 2-acetoxyphenylbutyl sulfide, 2-acetoxyphenylpentyl sulfide, 2-acetoxyphenylhexyl sulfide, 2-acetoxyphenylheptyl sulfide, 2-acetoxyphenyl-2-butoxyethyl sulfide, 2-acetoxyphenyl-2-trans-heptenyl sulfide, 2-acetoxyphenylhept-2-ynyl sulfide, 2-acetoxyphenylhex-2-ynyl sulfide, 2-acetoxyphenylpent-2-ynyl sulfide, 2-acetoxyphenylbut-2-ynyl sulfide and 2-acetoxyphenylprop-2-ynyl sulfide, or pharmaceutically acceptable salts or hydrates thereof.

Compounds of Formula (I) are capable of inhibiting inducible proinflammatory proteins, such as cyclooxygenase-2 and are therefore useful in therapy. These proinflammatory lipid mediators of the cyclooxygenase (CO) pathway are produced by the inducible cyclooxygenase-2 enzyme. Regulation, therefore, of cyclooxygenase-2 which is responsible for these products derived from arachidonic acid, such as the prostaglandins affect a wide variety of cells and tissue states and conditions. Expression of cyclooxygenase-1 is not affected by the compounds of Formula (I). This selective inhibition of cyclooxygenase-2 may alleviate or spare ulcerogenic liability associated with inhibition of cyclooxygenase-1 thereby inhibiting prostaglandins essential for cytoprotective effects. Thus, inhibition of the proinflammatory mediators is of benefit in controlling, reducing and alleviating many of these disease states. Most notably, prostaglandins have been implicated in pain (such as in the sensitization of pain receptors) or edema. This aspect of pain management includes treatment of neuromuscular pain, headache, cancer pain and arthritis pain. Compounds of Formula (I) or a pharmaceutically acceptable salt thereof, are of use in the prophylaxis or therapy in a human, or other mammal, by inhibition of the synthesis of the cyclooxygenase-2 enzyme.

Accordingly, the present invention is also directed to a method of inhibiting the synthesis of prostaglandins by inhibition of prostaglandin endoperoxide syntase-2 (PGHS-2) in a mammal in need of such treatment, comprising the step of administering to said mammal an effective amount of a compound of Formula (I). Generally, this method is useful in the prophylaxis or therapeutic treatment of edema, fever, algesia, neuromuscular pain, headache, cancer pain or arthritic pain. Representative compounds useful in this method include 2-acetoxythioanisole, 2-(trifluoromethylacetoxy)thioanisole, 2-($\alpha$-chloroacetoxy)thioanisole, 2-($\alpha$-bromoacetoxy)thioanisole, 2-acetoxyphenylbenzyl sulfide, 2-acetoxyphenyl-2-phenylethyl sulfide, 2-acetoxyphenylethyl sulfide, 2-acetoxyphenylpropyl sulfide, 2-acetoxyphenylbutyl sulfide, 2-acetoxyphenylpentyl sulfide, 2-acetoxyphenylhexyl sulfide, 2-acetoxyphenylheptyl sulfide, 2-acetoxyphenyl-2-butoxyethyl sulfide, 2-acetoxyphenyl-2-trans-heptenyl sulfide, 2-acetoxyphenylhept-2-ynyl sulfide, 2-acetoxyphenylhex-2-ynyl sulfide, 2-acetoxyphenylpent-2-ynyl sulfide, 2-acetoxyphenylbut-2-ynyl sulfide and 2-acetoxyphenylprop-2-ynyl sulfide, or pharmaceutically acceptable salts or hydrates thereof.

The present invention is also directed to a pharmaceutical composition, comprising a compound of Formula (I) and a pharmaceutically acceptable carrier or diluent. In order to a use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salt thereof and pharmaceutical compositions incorporating such, may be conveniently administered by any of the routes conventionally used for drug administration, e.g., orally, topically, parenterally, or by inhalation. The compounds of Formula (I) may be administered in conventional dosage forms prepared by combining a compound of Formula (I) with standard pharmaceutical carriers according to conventional procedures. The compounds of the present invention may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variable. The carrier(s) must be "acceptable" in the sense of being compatible with the other ingredients of the formulation and not deleterious to the recipient thereof.

The pharaceutical carrier employed may be, for example, either a solid or a liquid. Representative solid carriers are lactose, terra alba, sucrose, talc, gelatin, agar, pectin, acacia, magnesium sterate, stearic acid and the like. Representative liquid carriers include syrup, peanut oil, olive oil, water and the like. Similarly, the carrier may include time delay material well known in the art such as glyceryl monosterate or glyceryl disterarate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension.

Compounds of Formula (I) may be administered topically (non-systemically). This includes the application of a compound externally to the epidermis or the buccal cavity and the instillation of such a compound into the ear, eye and nose, such that the compound does not significantly enter the bloodstream. Formulation suitable for topical administration include liquid or semi-liquid preparations suitable for penetration through the skin to the site of inflammation such as liniments, lotions, creams, ointments, pastes and drops suitable for administration to the ear, eye and nose. The active ingredient may comprise, for topical administration from 0.001% to 10% w/w, for instance from 1% to 2% by weight of the Formulation. It may however, comprise as much as 10% w/w but preferably will comprise less than 5% w/w, more preferably from 0.1% to 1% w/w of the Formulation.

Lotions according to the present invention include those suitable for application to the skin and eye. An eye lotion may comprise a sterile aqueous solution optionally containing a bactericide and may be prepared by methods similar to those for the preparation of drops. Lotions or liniments for application to the skin may include an agent to hasten drying and to cool the skin, such as an alcohol or acetone, and/or a moisterizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap, a mucilage, an oil of natural origin such as almond, corn, archis, castor, or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving. Alternatively, the solution may be sterilized by filtration and transferred to the container by an aseptic technique. Examples of bactericidal and fungicidal agents suitable for inclusion in the drops are phenymercuric nitrate or acetate (~0.002%), benzalkonium chloride (~0.01%) and chlorhexidine acetate (~0.01%). Suitable solvents for the preparation of an oily solution include glycerol, diluted alcohol and propylene glycol.

Compounds of formula (I) may be administered parenterally, i.e., by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. Compounds may also be administered by inhalation, e.g., intranasal and oral inhalation administration. Appropriate dosage forms for such administration, such as aerosol formulation or a metered dose inhaler may be prepared by conventional techniques well known to those having ordinary skill in this art.

For all methods of use disclosed herein for the compounds of the present invention, the daily oral dosage regiment will preferably be from about 0.1 to about 100 mg/kg of total body weight. The daily parenteral dosage regiment will preferably be from about 0.1 to about 100 mg/kg of total body weight. The daily topical dosage regimen will preferably be from about 0.1 to about 15 mg, administered one to four, preferably two to three times daily. It will also be recognized by one of skill in this art that the optimal quantity and spacing of individual dosages of a compound of the present invention, or a pharmaceutically acceptable salt thereof, will be determined by the nature and extent of the condition being treated and that such optimums can be determined by conventional techniques.

Suitable pharmaceutically acceptable salts are well known to those skilled in the art and include basic salts of inorganic and organic acids, such as hydrochloric acid, hydrobromic acid, sulphuric acid, phophoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

The following examples are given for the purpose of illustrating various embodiments of the invention and are not meant to limit the present invention in any fashion.

EXAMPLE 1

Chemistry

Melting points were determined using a Gallenkamp melting point apparatus and are uncorrected. Tetrahydrofuran (THF) was distilled from sodium benzophenone ketyl. Acetonitrile was distilled over calcium hydride. Unless stated otherwise, synthetic reactions were carried out under a argon atmosphere. All chemicals (Aldrich, Milwaukee, Wis. or Lancaster, Pa.) were reagent grade or better. $^1$H NMR spectra were recorded on a Bruker WP-360 or AM 400 spectrometers; chemical shifts are expressed in parts per million relative to internal tetramethylsilane (TMS) standard and spin multiplicities are given as s (singlet), bs (broad singlet), d (doublet), dd (doublet of doublet), t (triplet), q (quartet), and m (multiplet). Fast atom bombardment mass spectra (FAB-MS) were recorded on a Kratos Concept II HH four sector mass spectrometer. Column chromatography was performed using silica gel (60–100 mesh) from fisher.

EXAMPLE 2

Synthesis of 2-Hydroxy-1-methylphenylsulfone (3)

To a reaction mixture containing 2-hydroxy-1-methylphenylmercaptan (1, 1 g, 7.13 mmol) in 20 mL of glacial acetic acid was added 30% $H_2O_2$ (14 mL) dropwise at 0° C. After the addition was complete, the reaction was warmed to 100° C. and allowed to stir overnight. The mixture was concentrated under reduced pressure and the residue was purified by chromatography on silica gel (EtOAc:pet ether; 90:10) and then recrystallized from EtOH/$H_2O$ to afford 3 as a white crystalline solid in 52% yield: mp 95–97° C.; $^1$H NMR (CDCl$_3$) δ 8.85 (s, 1H, OH), 7.67–7.71 (dd, 1H, ArH), 7.51–7.56 (t, 1H, ArH), 7.02–7.06 (m, 2H, ArH), 3.13 (s, SO$_2$CH$_3$). FAB-MS 173 (MH$^+$, 55), 157 (55), 93 (30), 79 (100) (FIG. 2B).

Figure 2A:
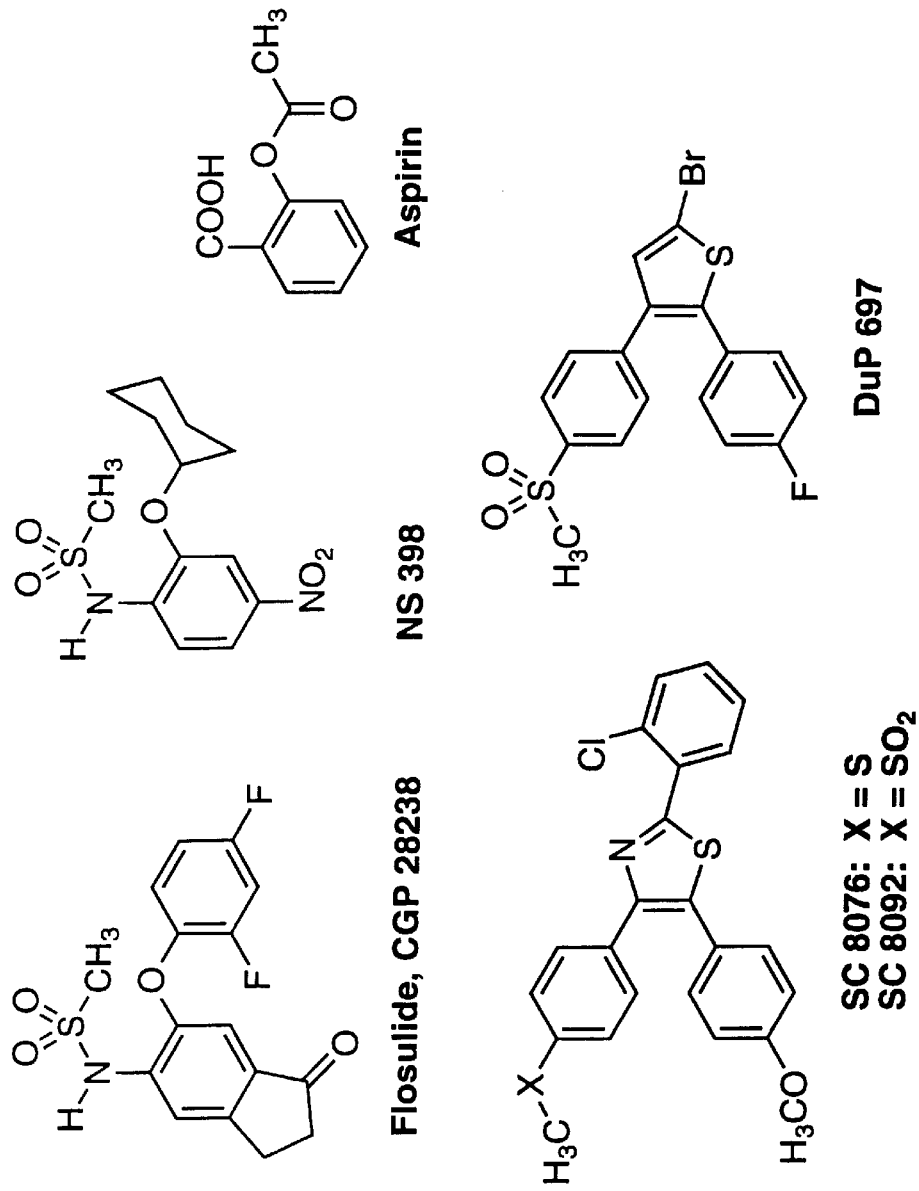
FIG. 2A shows the structures of flosulide, NS-398, SC 8076, aspirin and DuP 697.
Figure 2B:
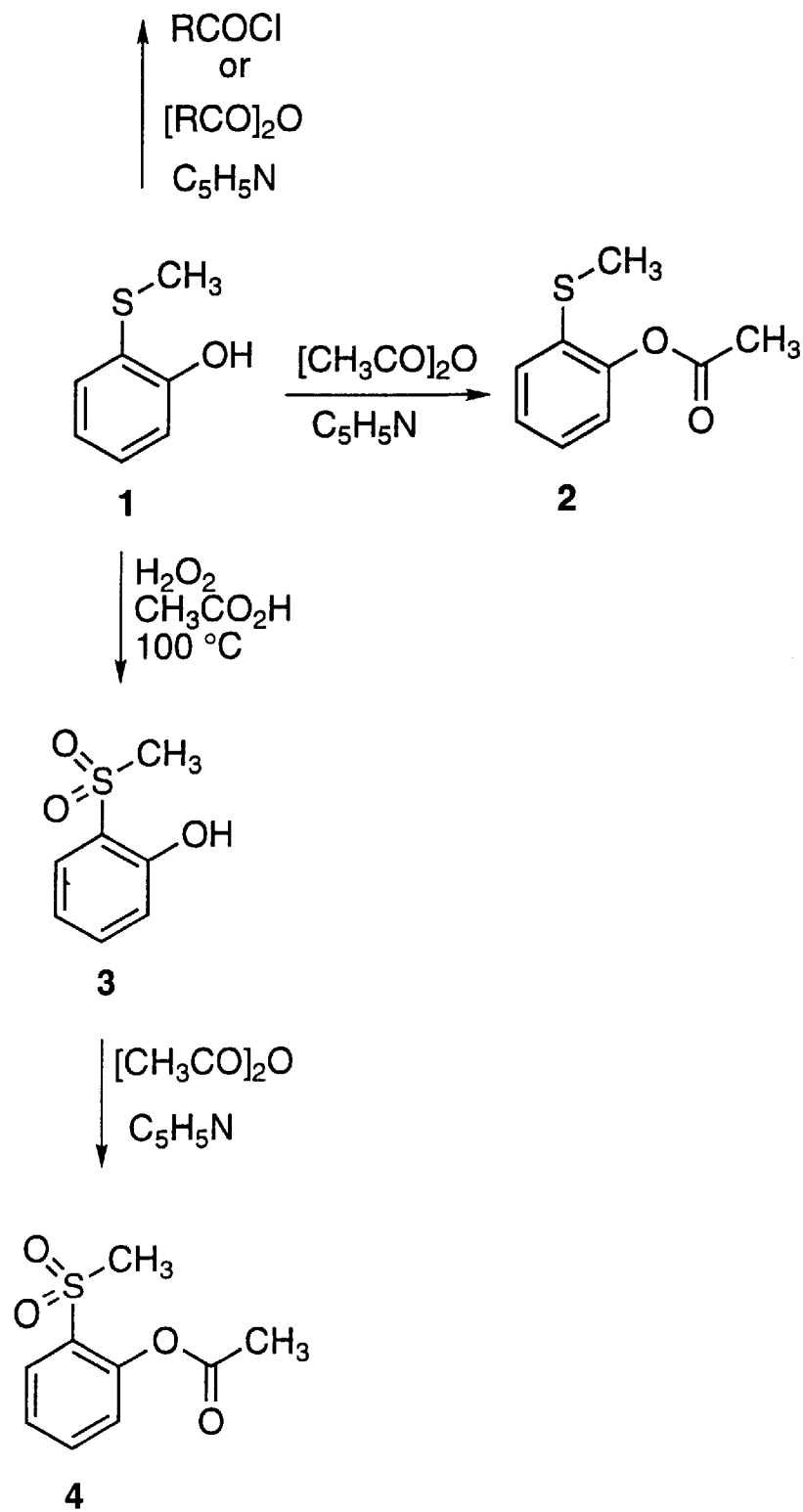
FIG. 2B shows the synthetic scheme for the synthesis of compounds 2, 3, 4 and 6–14.

2-Hydroxyphenylheptyl sulfone (92) was prepared in a similar manner as a colorless oil (137 mg, 62%). $^1$H NMR (CDCl$_3$) δ 7.62–7.64 (dd, 1H, ArH), 7.51–7.55 (t, 1H, ArH), 7.01–7.05 (m, 2H, ArH), 3.11–3.15 (t, 2H, CH$_2$), 1.70–1.78 (m, 2H, CH$_2$), 1.24–1.36 (m, 8H, CH$_2$), 0.84–0.87 (t, 3H, CH$_3$) (FIG. 2J).

EXAMPLE 3

Acetylation of the Phenol Derivatives; Method A

A reaction mixture containing appropriate arenol (14.26 mmol) in 5 mL of acetic anhydride and 5 drops of $H_3PO_4$ was heated on a water bath for 15 min. Water (10 mL) was added dropwise to the hot reaction mixture which was then cooled in an ice-bath. The aqueous solution was extracted with CHCl$_3$ (3×30 mL). The combined organic extracts were washed with water, dried (MgSO$_4$), filtered, and the solvent was removed under vacuo to afford the crude product which was purified on silica gel with EtOAc:petroleum ether (10:90) to afford the desired product in near quantitative yields.

2-Acetoxy-1-methylphenylsulfone (4) White crystalline solid from EtOH/$H_2O$ in 91% yield: mp 107–109° C.; $^1$H NMR (CDCl$_3$) δ 8.01–8.04 (dd, 1H, ArH), 7.65–7.68 (t, 1H, ArH), 7.41–7.46 (t, 1H, ArH), 7.25–7.28 (d, 1H, ArH), 3.12 (s, 3H, SO$_2$CH$_3$), 2.3 (s, 3H, COCH$_3$) (FIG. 2B).

2-Acetoxyanisole (5) Colorless oil in 78% yield. $^1$H NMR (CDCl$_3$) δ 7.02–7.05 (t, 1H, ArH), 6.94–6.98 (m, 3H, ArH), 3.83 (s, 3H, CH$_3$), 2.31 (s, 3H, CH$_3$); FAB-MS MH+167 (100), 124 (60), 79 (80).

EXAMPLE 4

Acetylation of the Phenol Derivatives: Method B

A reaction mixture containing 2-mercaptomethylphenol (1, 0.3 g, 2.14 mmol) in 5 mL of CH$_2$Cl$_2$ was treated with dry pyridine (0.169 g, 2.2 mmol) and appropriate acid anhydride (2.14 mmol). The reaction mixture was stirred overnight and then diluted with water. The aqueous solution was extracted with Et$_2$O (3–10 mL). The combined organic solution was washed with water, dried (MgSO$_4$), filtered, and the solvent was removed under vacuo. The crude product was chromatographed on silica gel and eluted with EtOAc:petroleum ether (2:98) to afford the desired product. In this manner, 2-acyloxythioanisole analogs 6–14 were synthesized (FIG. 2B).

2-Acetoxyphenylheptyl sulfone (93) colorless oil in 56% yield. $^1$H NMR (CDCl$_3$) δ 7.98–8.0 (dd, 1H, ArH), 7.65–7.69 (t, 1H, ArH), 7.41–7.45 (t, 1H, ArH), 7.24–7.26 (d, 1H, ArH), 3.21–3.25 (t, 2H, CH$_2$), 2.37 (s, 3H, COCH$_3$), 1.62–1.72 (m, 2H, CH$_2$), 1.24–1.38 (m, 8H, CH$_2$), 0.84–0.87 (t, 3H, CH$_3$); FAB-MS 299 (MH$^+$, 40), 257 (100), 79 (24) (FIG. 2J).

EXAMPLE 5

Synthesis of 2-(Methoxymethyleneoxy)thioanisole (15) (Method A)

Figure 2C:
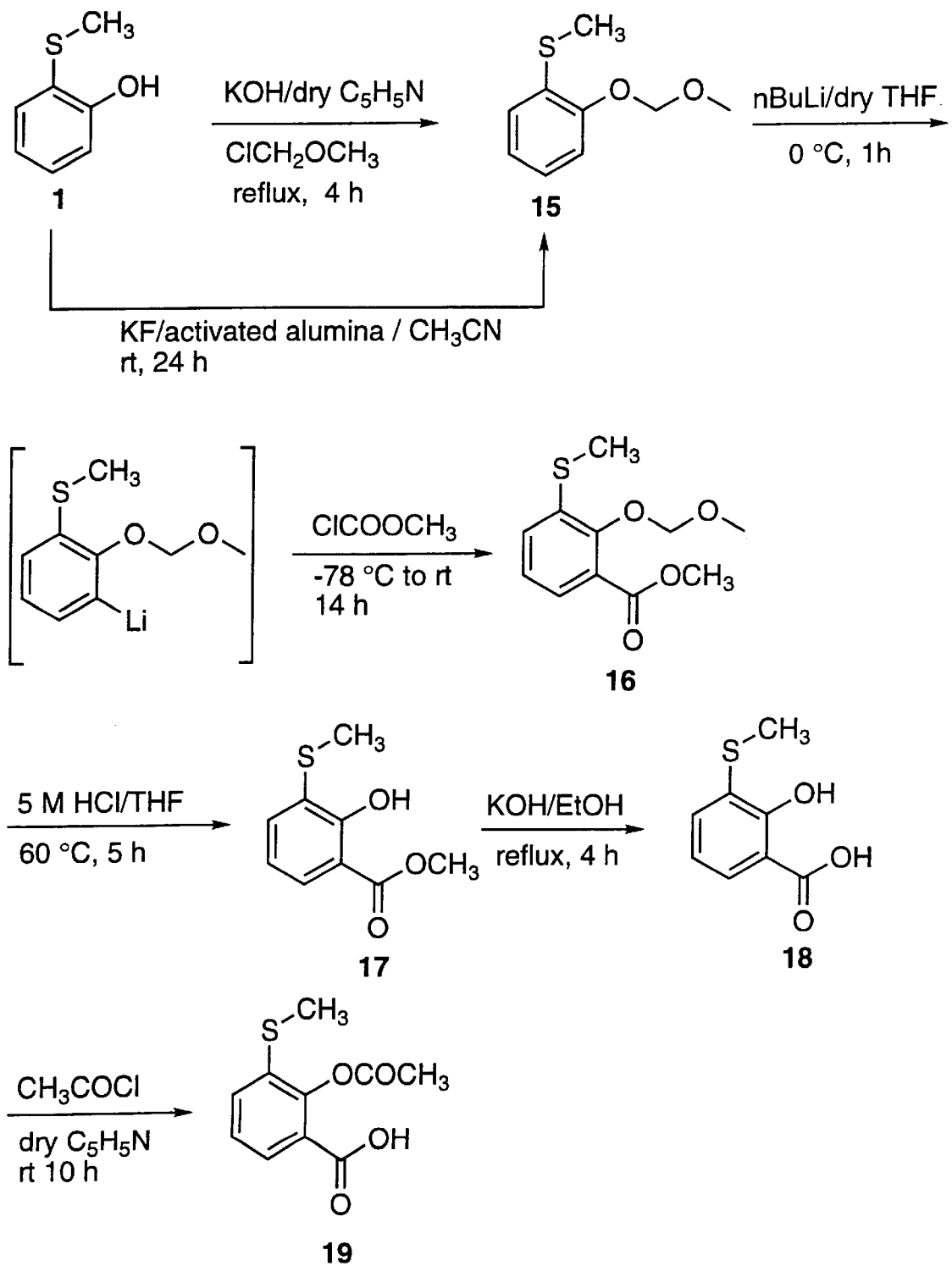
FIG. 2C shows the synthetic scheme for the synthesis of compounds 15, 16, 17, 18 and 19.

To a reaction mixture containing 2-hydroxythioanisole (1, 1 g, 7.14 mmol) in dry pyridine (0.3 g, 3.9 mmol) was added powdered KOH (0.4 g, 7.09 mmol) (FIG. 2C). The resulting solution was treated with methoxymethylchloride (0.72 g, 9.0 mmol), heated to reflux for 3.5 hours, cooled and partitioned between 1 M NaOH and diethyl ether. The organic solution was washed with 1 M HCl (2×30 mL), brine (50 mL), and then dried (MgSO$_4$). The solvent was removed under vacuo and the crude product was chromatographed on silica gel and eluted with petroleum ether:EtOAc (95:5) to afford the desired product as an colorless oil (1 g, 83%). $^1$H NMR (CDCl$_3$) δ7.01–7.17 (m, 4H, ArH), 5.25 (s, 2H, CH$_2$), 3.52 (s, 3H, OCH$_3$), 2.43 (s, 3H, SCH$_3$); FAB-MS 184 (MH$^+$ −1, 20), 167 (25), 149 (100).

EXAMPLE 6

Synthesis of 2-(Methoxymethyleneoxy)thioanisole (15) (Method B)

To a reaction mixture containing 2-hydroxythioanisole (1, 1 g, 7.14 mmol) in dry acetonitrile (30 mL) was added potassium fluoride activated alumina powder (8 g) and methoxymethylchloride (0.72 g, 9.0 mmol) (FIG. 2C). The mixture was stirred overnight at room temperature. The reaction mixture was filtered over celite and the solvent was evaporated under vacuo. The residue was partitioned between water and diethyl ether. The organic solution was washed with water and then dried (MgSO$_4$). The solvent was removed under vacuo and the crude product was chromatographed on silica gel and eluted with petroleum ether:EtOAc (95:5) to afford the desired product as an colorless oil (1.1 g, 85%).

EXAMPLE 7
Synthesis of 3-Methylmercapto-2-(methoxy)methyleneoxy-1-methyl benzoate (16)

To 2-(methoxy)methyleneoxy-1-thioanisole (15, 1.06 g, 5.7 mmol) in 30 mL of freshly distilled THF cooled in an ice bath was added n-BuLi (2.6 mL of 2.5 M solution in hexane, 6.27 mmol) and the reaction mixture was stirred at room temperature for 1 hour (FIG. 2C). The bright yellow solution was cooled to −78° C. and methylchloroformate (1.1 g, 11.7 mmol, 0.92 mL) was added all at once, and the mixture was then stirred at room temperature for 14 hours. The reaction mixture was quenched by the addition of saturated $NH_4Cl$ and the solution was concentrated under vacuo. The residue was diluted with water (50 mL) and extracted with $CH_2Cl_2$ (3×30 mL). The combined organic solution was washed with brine, water, and then dried ($MgSO_4$). The solvent was removed under reduced pressure and the residue was chromatographed on silica gel and eluted with petroleum ether/EtOAc 96:4 (starting material was recovered at this polarity) and then 90:10 to afford the desired product 16 as a oil (0.61 g, 44%). $^1$H NMR δ 7.55–7.58 (dd, 1H, ArH), 7.28–7.31 (dd, 1H, ArH), 7.13–7.18 (t, 1H, ArH), 5.1 (s, 2H, $CH_2$), 3.90 (s, 3H, $COOCH_3$), 3.63 (s, 3H, $OCH_3$), 2.44 (s, 3H, $SCH_3$); FAB-MS 243 ($MH^+$ −1, 30), 211 (100).

EXAMPLE 8
Synthesis of 3-(Methylmercapto)methylsalicylate (17)

A reaction mixture comprising of 16 (0.6 g, 2.47 mmol) in THF (0.23 mL), water (2 mL), and 6 M HCl (5 mL) was heated at 60° C. for 6 hours (FIG. 2C). The reaction mixture was poured into a equal volume of saturated NaCl and the aqueous solution was extracted with diethyl ether (3×20 mL). The combined organic solution was dried ($MgSO_4$), filtered and the solvent removed under vacuo. The crude product was chromatographed on silica gel and eluted with petroleum ether:EtOAc (95:5) to afford 17 as a crystalline white solid (0.3 g, 61%). $^1$H NMR ($CDCl_3$) δ 11.38 (s, 1H, OH), 7.65–7.69 (dd, 1H, ArH), 7.35–7.38 (dd, 1H, ArH), 6.86–6.91 (t, 1H, ArH), 3.96 (s, 3H, $OCH_3$), 2.46 (s, 3H, $SCH_3$); FAB-MS 199 ($MH^+$, 70), 198 ($M^+$ 95), 167 (100).

EXAMPLE 9
Synthesis of 3-(Methylmercapto)salicylic acid (18)

A reaction mixture containing the methylsalicylate derivative 17 (50 mg, 0.25 mmol), powdered KOH (56 mg, 1 mmol) in EtOH:$H_2O$ (3.64 mL:0.36 mL) was heated under reflux for 3.5 hours (FIG. 2C). The resultant solution was cooled and acidified with 1 M HCl. The aqueous solution was extracted with EtOAc (3×10 mL). The combined organic solution was washed with brine, water, and then dried ($MgSO_4$). The solvent was removed under reduced pressure to afford the essentially pure salicylic acid derivative 18 as a white solid (38 mg, 82%). $^1$H NMR (DMSO-$d_6$) δ 7.57–7.60 (d, 1H, ArH), 7.39–7.41 (d, 1H, ArH), 6.92–6.97 (t, 1H, ArH), 2.41 (s, 3H, $SCH_3$); FAB-MS 185 ($MH^+$, 20), 184 ($MH^+$ −1, 20), 167 (75), 102 (70), 79 (100).

EXAMPLE 10
Synthesis of 3-(Methylmercapto)acetylsalicyclic acid (19)

Figure 2D:
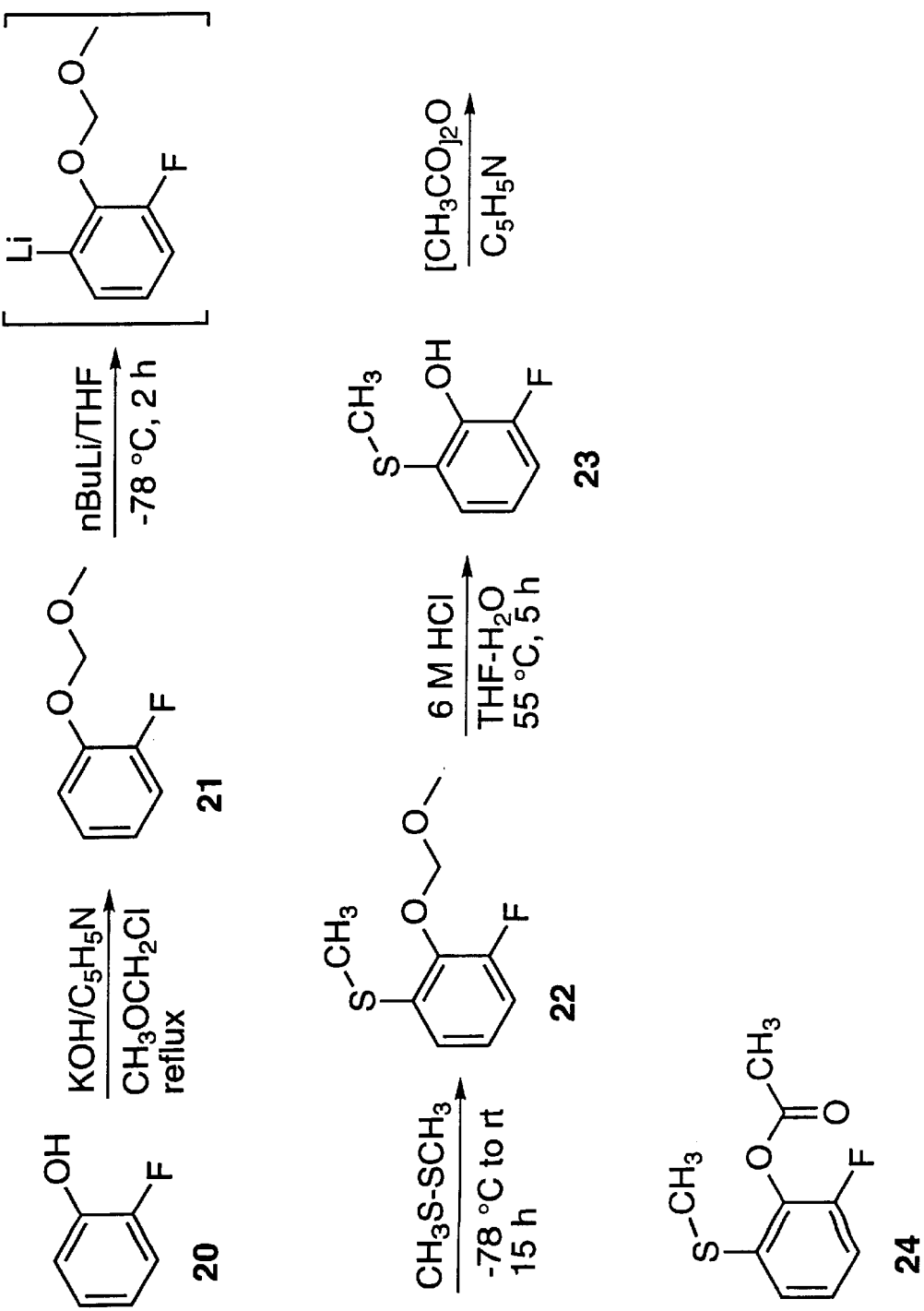
FIG. 2D shows the synthetic scheme for the synthesis of compounds 21, 22, 23, and 24.

To solution of 18 (46 mg, 0.25 mmol) in 1 mL of $CH_2Cl_2$ was added dry pyridine (20 mg, 50 μL, 0.3 mmol) at 0° C. (FIG. 2D). The solution was stirred at 0° C. for 10 minutes followed by the addition of acetyl chloride (~30 μL, 0.4 mmol). The reaction mixture was stirred overnight at 0° C. and then the solvent was removed under vacuo. The residue was partioned between water and EtOAc. The organic solution was washed with 1 M HCl (10 mL), water (50 mL), and then dried ($MgSO_4$). The solvent was evaporated to afford a oil which was chromatographed on silica gel and eluted with hexanes:EtOAc (initially 70:30, then 50:50) to afford the desired product as a white solid (11 mg, 20% yield). $^1$H NMR ($CDCl_3$) δ 7.86–7.89 (d, 1H, ArH), 7.46–7.44 (d, 1H, ArH), 7.32–7.36 (t, 1H, ArH), 2.45 (s, 3H, $SCH_3$), 2.38 (s, 3H, $CH_3$); FAB-MS 227 ($MH^+$, 15) 226 ($MH^+$ −1, 10), 167 (50), 157 (30), 102 (100).

EXAMPLE 11
Synthesis of 2-Fluoro-1-methoxymethylphenol (21)

To a reaction mixture containing 2-fluorophenol (20, 2 g, 17.84 mmol) in 30 mL of dry pyridine was added powdered KOH (1 g, 17.71 mmol) and methoxymethyl chloride (1.8 g, 22.49 mmol) and this reaction mixture was heated under reflux for 3.5 hours (FIG. 2D). The reaction was cooled and partitioned between 1 M NaOH and ethyl ether (2×30 mL). The organic solution was washed with 1 M HCl (2×20 mL), water, and then dried ($MgSO_4$), filtered, and the solvent removed under vacuo to afford a oily residue. The crude product was purified by column chromatography (EtOAc:hexanes; 5:95) to afford the desired product as a pale yellow oil in 62% yield. $^1$H NMR ($CDCl_3$) δ 6.95–7.22 (m, 4H, ArH), 5.21 (s, 2H, $CH_2$), 3.52 (s, 3 H, $CH_3$).

EXAMPLE 12
Synthesis of 3-Fluoro-2-methoxymethyleneoxyphenylmethyl sulfide (22)

A flame-dried 3-necked flask was charged with 2-fluoro-1-methoxymethylphenol (21, 1.07 g, 6.4 mmol) in 30 mL of freshly distilled THF under argon and this mixture was cooled to −78° C. (FIG. 2D). nBuLi (2.5 M solution in hexane, 3 mL, 7.25 mmol) was added to this reaction mixture which was allowed to stir at −78 ° C. for 2.5 hours under argon. Methyldisulfide (0.68 g, 7.25 mmol) was then added to the mixture at −78° C. and then the acetone/dry ice bath was removed and the reaction was allowed to proceed at room temperature for 20 hours. Sat. $NH_4Cl$ (~20 mL) was added to the mixture which was then stirred for an additional 10 min and then extracted with ethyl ether (3×10 mL). The combined organic solution was washed with brine, water and then dried ($MgSO_4$) and filtered. The solvent was removed under vacuo to afford the crude product which was purified by flash chromatography on silica gel (EtOAc:hexanes; 5:95) to yield a yellow oil (0.8 g, 79%). $^1$H NMR ($CDCl_3$) δ 7.0–7.04 (m, 1H, ArH), 6.89–6.92 (m, 2H, ArH), 5.18 (s, 2H, $CH_2$), 3.64 (s, 3H, $CH_3$), 2.44 (s, 3H, $CH_3$).

EXAMPLE 13
Synthesis of 3-Fluoro-2-hydroxyphenylmethyl sulfide (23)

A reaction mixture containing the MOM-protected phenol (22, 0.57 g, 2.8 mmol) and 6 M HCl (~5 mL) in 10% THF-$H_2O$ (2 mL) was heated at 60° C. for 5 hours (FIG. 2D). Sat. NaCl was added to the reaction mixture and the aqueous solution was extracted with ethyl ether (3×10 mL). The combined organic solution was washed with water, dried ($MgSO_4$), filtered and the solvent removed under vacuo to afford a oily residue. The product was purified by flash chromatography (5% EtOAc:hexanes) to yield a pale yellow oil (190 mg, 46%). $^1$H NMR ($CDCl_3$) δ 7.17–7.21 (dd, 1H, ArH), 7.0–7.06 (m, 1 H, ArH), 6.79–6.86 (m, 1H, ArH), 6.23–6.24 (d, 1H, OH), 2.38 (s, 3H, $CH_3$).

EXAMPLE 14
Synthesis of 2-Acetoxy-3-fluorophenylmethyl sulfide (24)

To a solution containing the phenol derivative (23, 140 mg, 0.9 mmol) in $CH_2Cl_2$ (2 mL) was added dry pyridine (74 mg, 0.92 mmol) and acetic anhydride (74 mg, 0.92 mmol) and the reaction mixture was allowed to stir overnight at room temperature (FIG. 2D). The solvent was removed under reduced pressure and diluted with water. The aqueous solution was extracted with ethyl ether (2× 10 mL) and the ethereal extracts were dried (MgSO$_4$), filtered, and the solvent evaporated. Column chromatography (10% EtOAc:hexanes) of the crude product gave the pure acetoxy derivative as a colorless oil (104 mg, 60%). $^1$H NMR (CDCl$_3$) δ 7.14–7.18 (m, 1H, ArH), 6.96–7.02 (m, 2H, ArH), 2.44 (s, 3H, CH$_3$), 2.37 (s, 3H, COCH$_3$).

EXAMPLE 15
Synthesis of 2,4-difluoro-1-methoxymethylphenol (26)

Figure 2E:
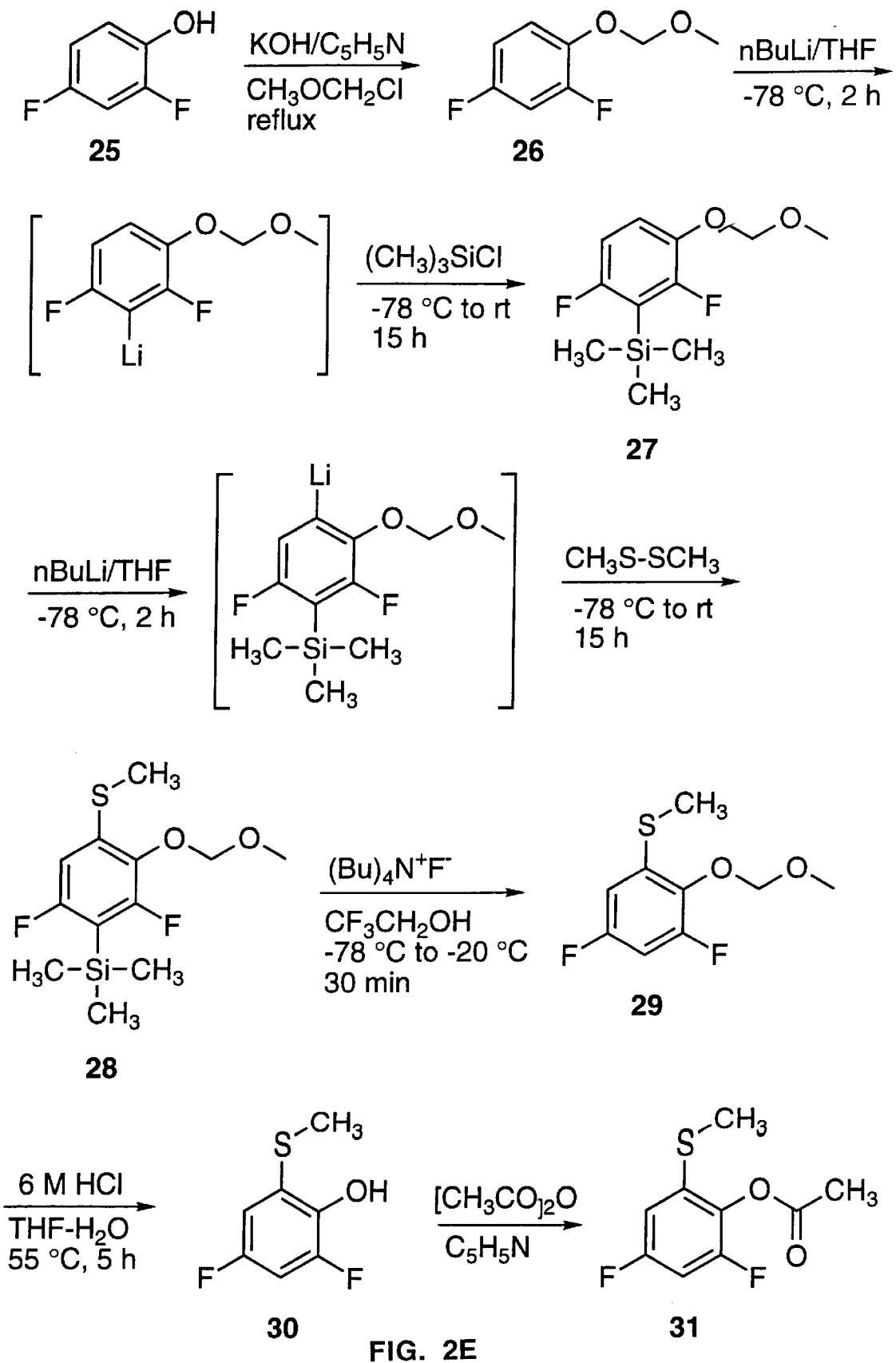
FIG. 2E shows the synthetic scheme for the synthesis of compounds 26, 27, 28, 29, 30 and 31.

To a reaction mixture containing 2,4-difluorophenol (25, 2 g, 15.37 mmol) in 30 mL of dry pyridine was added powdered KOH (0.854 g, 15.25 mmol) and methoxymethyl chloride (1.6 g, 19.37 mmol) and this reaction mixture was heated under reflux for 3.5 hours (FIG. 2E). The reaction was cooled and partitioned between 1 M NaOH and ethyl ether (2×30 mL). The organic solution was washed with 1 M HCl (2×20 mL), water, and then dried (MgSO$_4$), filtered, and the solvent removed under vacuo to afford a oily residue. The crude product was purified by column chromatography (EtOAc:hexanes; 5:95) to afford the desired product as a pale yellow oil in 71% yield. $^1$H NMR (CDCl$_3$) δ 7.1–7.16 (m, 1H, ArH), 6.78–6.88 (m, 2H, ArH), 5.15 (s, 2H, CH$_2$), 3.52 (s, 3H, CH$_3$).

EXAMPLE 16
Synthesis of 2,4-Difluoro-3-trimethylsilyl-1-methoxymethylphenol (27)

A flame-dried 3-necked flask was charged with 2,4-difluoro-1-methoxymethylphenol (26, 0.84 g, 4.8 mmol) in 30 mL of freshly distilled THF under argon and this mixture was cooled to –78° C. (FIG. 2E). nBuLi (2.5 M solution in hexane, 2.2 mL, 5.43 mmol) was added to this reaction mixture which was allowed to stir at –78° C. for 2.5 hours under argon. Chlorotrimethyl silane (1.0 M solution in THF, 5.43 mL, 5.43 mmol) was then added to the deep pink colored mixture at –78° C. and then the acetone/dry ice bath was removed and the reaction was allowed to proceed at room temperature for 14 h. Sat. NH$_4$Cl (~20 mL) was added to the mixture which was then stirred for an additional 10 minutes and then extracted with ethyl ether (3×10 mL). The combined organic solution was washed with brine, water and then dried (MgSO$_4$) and filtered. The solvent was removed under vacuo to afford the crude product which was purified by flash chromatography on silica gel (EtOAc:hexanes; 5:95) to yield a yellow oil (0.8 g, 79%). $^1$H NMR (CDCl$_3$) δ 7.09–7.17 (m, 1H, ArH), 6.68–6.74 (m, 1H, ArH), 5.13 (s, 2H, CH$_2$), 3.52 (s, 3H, CH$_3$), 0.36–0.37 (t, 9H, Si(CH$_3$)$_3$); FAB-MS 247 (MH$^+$, 70), 229 (40), 219 (60), 189 (58), 157 (40), 133 (60), 79 (100).

EXAMPLE 17
Synthesis of 2,4-Difluoro-6-methylmercapto-3-trimethylsilyl-1-methoxymethyl phenol (28)

A flame-dried 3-necked flask was charged with 2,4-difluoro-3-trimethylsilyl-1-methoxymethylphenol (27, 0.63 g, 2.56 mmol) in 15 mL of freshly distilled THF under argon and this mixture was cooled to δ 78° C. (FIG. 2E). nBuLi (2.5 M solution in hexane, 1.16 mL, 2.9 mmol) was added to this reaction mixture which was allowed to stir at –78° C. for 2.5 h under argon. Methyldisulfide (0.27 g, 2.9 mmol) was then added to the mixture at –78° C. and then the acetone/dry ice bath was removed and the reaction was allowed to proceed at room temperature for 14 hours. Sat. NH$_4$Cl (~10 mL) was added to the mixture which was then stirred for an additional 10 min and then extracted with ethyl ether (3×10 mL). The combined organic solution was washed with brine, water and then dried (MgSO$_4$) and filtered. The solvent was removed under vacuo to afford the crude product which was purified by flash chromatography on silica gel (EtOAc:hexanes; 5:95) to yield a yellow oil (0.51 g, 68%). $^1$H NMR (CDCl$_3$) δ 6.55–6.58 (dd, 1H, ArH), 5.09 (s, 2H, CH$_2$), 3.63 (s, 3H, CH$_3$), 2.41 (s, 3H, CH$_3$), 0.34–0.35 (t, 9 H, Si(CH$_3$)$_3$); FAB-MS 293 (MH+, 24), 292 (M+, 70), 262 (66), 261 (100).

EXAMPLE 18
Synthesis of 2,4-Difluoro-6-methylmercapto-1-methoxy methyl phenol (29)

A reaction mixture containing the trimethylsilyl derivative (28, 0.51 g, 1.74 mmol) in 10 mL of freshly distilled THF was treated with trifluoroethanol (0.18 g, 1.82 mmol) and tetrabutylammonium fluoride (1 M solution in THF, 1.74 mL, 1.74 mmol) at –78° C. under argon (FIG. 2E). The reaction mixture was allowed to stir at –78° C. for 20 min and at room temperature for 30 minutes. The reaction was quenched by the addition of water, followed by extraction with ethyl ether (2×15 mL). The combined organic extracts were washed with water, dried (MgSO$_4$), filtered, and the solvent removed under vacuo. Silica gel chromatography (5% EtOAc:hexanes) gave the pure product as a colorless oil (270 mg, 71%). $^1$H NMR (CDCl$_3$) δ 6.6–6.64 (m, 2H, ArH), 5.11 (s, 2H, CH$_2$), 3.63 (s, 3H, CH$_3$), 2.42 (s, 3H, CH$_3$).

EXAMPLE 19
Synthesis of 3,5-Difluoro-2-hydroxyphenylmethyl sulfide (30)

Figure 2F:
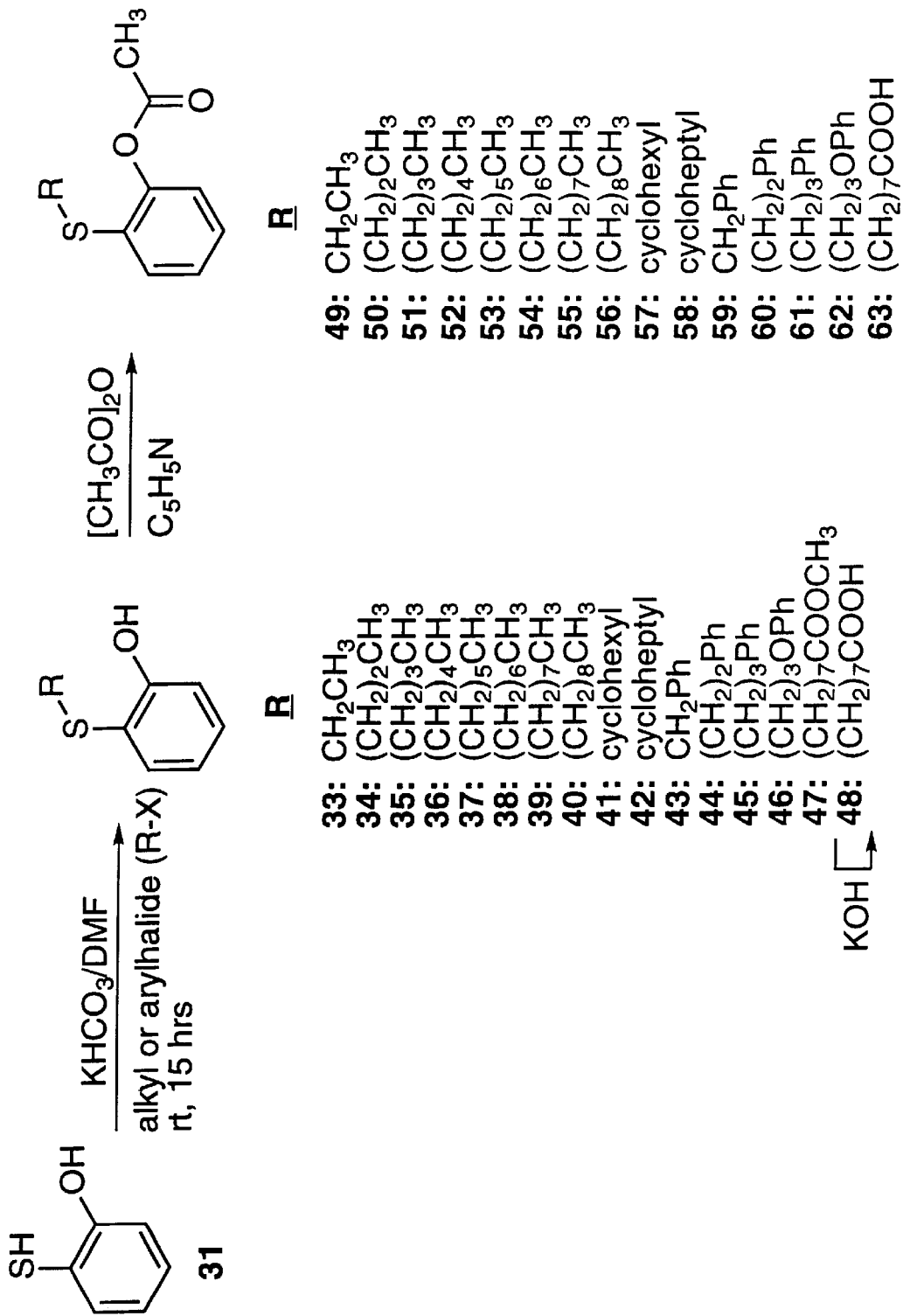
FIG. 2F shows the synthetic scheme for the synthesis of compounds 33–48 and 49–63.

A reaction mixture containing the MOM-protected phenol (29, 270 mg, 1.22 mmol) and 6 M HCl (~1 mL) in 10% THF-H$_2$O (1 mL) was heated at 60° C. for 4 hours (FIG. 2F). Sat. NaCl was added to the reaction mixture and the aqueous solution was extracted with ethyl ether (3×10 mL). The combined organic solution was washed with water, dried (MgSO$_4$), filtered and the solvent removed under vacuo to afford a oily residue. The product was purified by flash chromatography (5% EtOAc:hexanes) to yield a pale yellow oil (110 mg, 53%). $^1$H NMR (CDCl$_3$) δ 6.87–6.91 (m, 1H, ArH), 6.75–6.82 (m, 1H, ArH), 5.85 (d, 1H, OH), 2.41 (s, 3H, CH$_3$).

EXAMPLE 20
Synthesis of 2-Acetoxy-3,5-difluorophenylmethyl sulfide (31)

A reaction mixture consisting of the phenol derivative (30, 110 mg, 0.62 mmol), dry pyridine (58 mg, 0.64 mmol) and acetic anhydride (63 mg, 0.63 mmol), in CH$_2$Cl$_2$ (2 mL) was allowed to stir overnight at room temperature (FIG. 2E). The solvent was removed under reduced pressure and diluted with water. The aqueous solution was extracted with ethyl ether (2×10 mL) and the ethereal extracts were dried (MgSO$_4$), filtered, and the solvent evaporated. Column chromatography (5% EtOAc:hexanes) of the crude product gave the pure acetoxy derivative as a colorless oil (75 mg, 56%). $^1$H NMR (CDCl$_3$) δ 6.67–6.73 (m, 2H, ArH), 2.43 (s, 3H, CH$_3$), 2.36 (s, 3H, COCH$_3$); FAB-MS 219 (MH$^+$, 28), 218 (M$^+$, 30), 176 (84), 157 (70), 149 (42), 121 (46), 79 (100).

EXAMPLE 21
Synthesis of the 2-Hydroxyphenylalkyl Sulfides

A reaction mixture containing 2-hydroxythiophenol (32, 3.96 mmol) in 4 mL of dry DMF was treated with KHCO$_3$ (4.52 mmol) and alkyl halide (3.96 mmol) and allowed to stir at room temperature overnight (FIG. 2F). The reaction mixture was diluted with water and extracted with ethyl ether (3×20 mL). The combined organic extracts were washed with water (2×50 mL), dried (MgSO$_4$), filtered, and the solvent removed under vacuo. The residue was chromatographed on silica gel and eluted with EtOAc:hexanes (3:97) to afford the desired products.

2-Hydroxyphenylethyl sulfide (33) colorless oil in 60% yield. $^1$H NMR (CDCl$_3$) δ 7.44–7.48 (dd, 1H, ArH), 7.23–7.28 (m, 1H, ArH), 6.9–7.0 (dd, 1H, ArH), 6.84–6.89 (m, 1H, ArH), 6.7 (s, 1H, OH), 2.67–2.75 (q, 2H, CH$_2$), 1.19–1.24 (t, 3H, CH$_3$).

2-Hydroxyphenylpropyl sulfide (34) colorless oil in 77% yield. $^1$H NMR (CDCl$_3$) δ 7.44–7.47 (dd, 1H, ArH), 7.22–7.26 (m, 1H, ArH), 6.96–6.99 (dd, 1H, ArH), 6.83–6.89 (t, 1H, ArH), 6.76 (s, 1H, OH), 2.64–2.69 (t, 2H, CH$_2$), 1.55–1.61 (m, 2H, CH$_2$), 0.95–1.0 (t, 3H, CH$_3$); FAB-MS MH+ 169 (25), M$^+$ 168 (60), 93 (22), 79 (100).

2-Hydroxyphenyl-2-methylpropyl sulfide (35) colorless oil in 78% yield. $^1$H NMR (CDCl$_3$) δ 7.44–7.47 (dd, 1H, ArH), 7.21–7.25 (m, 1H, ArH), 6.96–6.99 (dd, 1H, ArH), 6.83–6.88 (t, 1H, ArH), 6.74 (s, 1H, OH), 2.58–2.60 (dd, 2H, CH$_2$), 1.71–1.78 (m, 1H, CH), 0.99–1.01 (d, 6H, CH$_3$).

2-Hydroxyphenylpentyl sulfide (36) colorless oil in 89% yield. $^1$H NMR (CDCl$_3$) δ 7.44–7.47 (dd, 1H, ArH), 7.22–7.28 (m, 1H, ArH), 6.96–6.99 (dd, 1H, ArH), 6.83–6.89 (t, 1H, ArH), 6.75 (s, 1H, OH), 2.65–2.70 (t, 2H, CH$_2$), 1.5–1.58 (m, 2H, CH$_2$), 1.25–1.37 (m, 4H, CH$_2$), 0.84–0.91 (t, 3H, CH$_3$).

2-Hydroxyphenylhexyl sulfide (37) colorless oil in 84% yield. 1H NMR (CDCl$_3$) δ 7.44–7.47 (dd, 1H, ArH), 7.22–7.28 (m, 1H, ArH), 6.96–6.99 (dd, 1H, ArH), 6.83–6.89 (t, 1H, ArH), 6.75 (s, 1H, OH), 2.65–2.70 (t, 2H, CH$_2$), 1.5–1.59 (m, 2H, CH$_2$), 1.22–1.41 (complex multiplet, 6H, CH$_2$), 0.84–0.89 (t, 3H, CH$_3$).

2-Hydroxyphenylheptyl sulfide (38) colorless oil in 67% yield. $^1$H NMR (CDCl$_3$) δ 7.44–7.47 (dd, 1H, ArH), 7.22–7.28 (m, 1H, ArH), 6.96–6.99 (dd, 1H, ArH), 6.83–6.89 (m, 1H, ArH), 6.75 (s, 1H, OH), 2.65–2.70 (t, 2H, CH$_2$), 1.5–1.59 (m, 2H, CH$_2$), 1.25–1.35 (complex multiplet, 8H, CH$_2$), 0.84–0.88 (t, 3H, CH$_3$).

2-Hydroxyphenyloctyl sulfide (39) colorless oil in 77% yield. 1H NMR (CDCl$_3$) δ 7.44–7.47 (dd, 1H, ArH), 7.22–7.28 (m, 1H, ArH), 6.96–6.99 (dd, 1H, ArH), 6.83–6.89 (m, 1H, ArH), 6.75 (s, 1H, OH), 2.65–2.70 (t, 2H, CH$_2$), 1.5–1.59 (m, 2H, CH$_2$), 1.24–1.38 (complex multiplet, 10H, CH$_2$), 0.84–0.88 (t, 3H, CH$_3$).

2-Hydroxyphenylnonyl sulfide (40) colorless oil in 69% yield. $^1$H NMR (CDCl$_3$) δ 7.44–7.47 (dd, 1H, ArH), 7.23–7.26 (m, 1H, ArH), 6.97–6.99 (dd, 1H, ArH), 6.84–6.88 (m, 1H, ArH), 6.75 (s, 1H, OH), 2.66–2.70 (t, 2H, CH$_2$), 1.54–1.56 (m, 2H, CH$_2$), 1.33–1.37 (m, 2H, CH$_2$), 1.24–1.28 (complex multiplet, 10H, CH$_2$), 0.85–0.89 (t, 3H, CH$_3$).

2-Hydroxyphenylcyclohexyl sulfide (41) colorless oil in 66% yield. $^1$H NMR (CDCl$_3$) δ 7.42–7.48 (dd, 1H, ArH), 7.24–7.29 (m, 1H, ArH), 6.97–7.03 (dd, 1H, ArH), 6.8–7.0 (m, 2H, ArH & OH), 2.75–2.85 (m, 1H, CH), 1.90–1.94 (m, 2H, CH$_2$), 1.74–1.77 (m, 2H, CH$_2$), 1.15–1.68 (m, 6H, CH$_2$).

2-Hydroxyphenylcycloheptyl sulfide (42) colorless oil in 66% yield. $^1$H NMR (CDCl$_3$) δ 7.43–7.45 (dd, 1H, ArH), 7.24–7.29 (m, 1 H, ArH), 6.97–7.0 (dd, 1H, ArH), 6.83–6.88 (m, 3H, ArH & OH), 2.97–3.05 (m, 1H, CH), 1.40–2.27 (m, 12H, CH$_2$).

2-Hydroxyphenylbenzyl sulfide (43) white solid in 66% yield. $^1$H NMR (CDCl$_3$) δ 7.21–7.27 (m, 5H, ArH), 7.06–7.09 (m, 2H, ArH), 6.90–6.93 (dd, 1H, ArH), 6.77–6.82 (m, 1H, ArH), 6.52 (s, 1H, OH), 3.84 (s, 2H, CH$_2$).

2-Hydroxyphenyl-2-phenethyl sulfide (44): colorless oil in 78% yield. $^1$H NMR (CDCl$_3$) δ 7.46–7.49 (dd, 1H, ArH), 7.27–7.30 (m, 3H, ArH), 7.13–7.15 (d, 2H, ArH), 6.98–7.01 (d, 1H, ArH), 6.88–6.90 (t, 1H, ArH), 6.64 (s, 1H, OH), 2.94–2.98 (m, 2H, CH$_2$), 2.82–2.86 (t, 2H, CH$_2$).

2-Hydroxyphenyl-3-phenylpropyl sulfide (45): colorless oil in 79% yield. $^1$H NMR (CDCl$_3$) δ 7.43–7.46 (dd, 1H, ArH), 7.12–7.29 (m, 6H, ArH), 6.97–6.99 (dd, 1H, ArH), 6.83–6.88 (m, 1H, ArH), 6.72 (s, 1H, OH), 2.67–2.72 (m, 4H, CH$_2$), 1.82–1.92 (m, 2H, CH$_2$).

2-Hydroxyphenyl-3-phenoxypropyl sulfide (46): colorless oil in 72% yield. $^1$H NMR (CDCl$_3$) δ 7.46–7.48 (dd, 1H, ArH), 7.24–7.29 (m, 3H, ArH), 6.84–6.98 (m, 5H, ArH), 4.01–4.05 (t, 2H, CH$_2$), 2.88–2.92 (t, 2H, CH$_2$), 1.99–2.06 (m, 2H, CH$_2$).

2-Hydroxyphenyl-8-(methoxycarbonyl)heptyl sulfide (47): colorless oil in 53% yield. $^1$H NMR (CDCl$_3$) δ 7.43–7.46 (dd, 1H, ArH), 7.23–7.28 (m, 1H, ArH), 6.96–6.99 (dd, 1H, ArH), 6.86–6.87 (m, 1H, ArH), 6.74 (s, 1H, ArOH), 3.66 (s, 3H, CH$_3$), 2.65–2.70 (t, 2H, CH$_2$), 2.26–2.31 (t, 2H, CH$_2$), 1.52–1.62 (m, 4H, CH$_2$), 1.26–1.39 (m, 6 H, CH$_2$); FAB-MS 283 (MH$^+$, 30), 282 (M$^+$, 100), 251 (40), 139 (34), 79 (50).

EXAMPLE 23

Synthesis of 2-Hydroxyphenyl-8-(carboxy)heptyl sulfide (48)

To a reaction flask containing (47, 0.5 g, 1.77 mmol) in a EtOH:H$_2$O (36mL:4mL) mixture was added powdered KOH (0.4 g, 7.08 mmol) and this reaction was heated under reflux for 3.5 hours. The solvent was removed under vacuo and the residue was diluted with 1 M HCl (pH ~2). The aqueous mixture was extracted with EtOAc (3×20 mL). The combined organic solution was washed with brine, water, and then dried (MgSO$_4$). The solvent was removed under reduced pressure to afford essentially pure carboxylic acid as an oil (89%). $^1$H NMR (CDCl$_3$) δ 7.43–7.46 (dd, 1H, ArH), 7.22–7.28 (m, 1H, ArH), 6.96–6.99 (dd, 1H, ArH), 6.84–6.89 (m, 1H, ArH), 6.74 (s, 1H, ArOH), 2.65–2.70 (t, 2H, CH$_2$), 2.31–2.36 (t, 2H, CH$_2$), 1.5–1.66 (m, 4 H, CH$_2$), 1.19–1.41 (m, 6H, CH$_2$).

EXAMPLE 24

Synthesis of 2-Hydroxyphenyl-2-butoxyethyl sulfide (66)

To a flame-dried flask containing 2-butoxyethanol (64, 0.5 g, 4.23 mmol) in 10 mL of dry THF was added triphenylphosphine (2.66 g, 10.15 mmol), dry pyridine (0.39 g, 4.9 mmol) and carbon tetrabromide (1.4 g, 4.23 mmol) (FIG. 2G). After stirring for 1 hour at room temperature, the reaction mixture was treated with hexanes and the precipitate was filtered. The filtrate was concentrated under reduced pressure and the residue was treated with 1 M HCl. The aqueous solution was extracted with hexanes (3×10 mL). The combined organic solution was washed with water, dried (MgSO$_4$), filtered, and the solvent evaporated under vacuo to afford a oil. $^1$H NMR analysis revealed the oil to be a mixture of starting alcohol 64 and the desired 2-butoxyethyl bromide (65) and was used in the subsequent reaction without further purification. To a reaction mixture containing 2-hydroxythiophenol (32, 100 mg, 0.8 mmol) in 1 mL of dry DMF was added KHCO$_3$ (95 mg, 0.95 mmol) and the crude 2-butoxyethyl bromide and this reaction mixture was stirred overnight at room temperature. The reaction was diluted with water and extracted with ethyl ether (2×10 mL). The organic solution was washed with water, dried (MgSO$_4$), filtered, and the solvent evaporated under vacuo to afford a oil. The crude phenol was chromatographed on silica gel (EtOAc:hexanes; 2:98) to afford the desired phenol 66 (34% yield based on starting 2-hydroxythiophenol). $^1$H NMR (CDCl$_3$) δ 7.46–7.49 (dd, 1H, ArH), 7.24–7.29 (m, 1H, ArH), 7.41 (s, 1H, OH), 6.96–6.99 (dd, 1H, ArH), 6.81–6.87 (m, 1H, ArH), 3.45–3.5 (m, 4H, CH$_2$), 2.86–2.90 (t, 2H, CH$_2$), 1.52–1.63 (m, 2H, CH$_2$), 1.33–1.45 (m, 2 H, CH$_2$), 0.88–0.96 (t, 3H, CH$_3$).

2-Hydroxyphenyl-3-ethoxypropyl sulfide (70): was prepared in a similar manner as described above in 67% yield (FIG. 2G). $^1$H NMR (CDCl$_3$) δ 7.45–7.47 (dd, 1H, ArH), 7.23–7.28 (dd, 1H, ArH), 6.97–6.99 (dd, 1H, ArH), 6.84–6.89 (s and d of t, 2H, OH & ArH), 3.43–3.51 (m, 4H, CH$_2$), 2.77–2.81 (t, 2H, CH$_2$), 1.77–1.84 (m, 2H, CH$_2$), 1.17–1.20 (t, 3H, CH$_3$).

2-Hydroxyphenyl-trans-hept-2-enyl sulfide (74): was prepared in a similar manner as described above in 54% yield (FIG. 2I). $^1$H NMR (CDCl$_3$) δ 7.39–7.42 (dd, 1H, ArH), 7.22–7.27 (m, 1H, ArH), 6.95–6.97 (dd, 1H, ArH), 6.82–6.87 (d of t, 1H, ArH), 6.7 (s, 1H, OH), 5.36–5.46 (m, 1H, olefinic H), 5.19–5.29 (m, 1H, olefinic H), 3.46–3.49 (d, 2H, CH$_2$), 1.66–1.93 (m, 2H, CH$_2$), 1.18–1.39 (m, 4H, CH$_2$), 0.82–0.94 (t, 3H, CH$_3$).

2-Hydroxyphenyl-hept-2-ynyl sulfide (82): was prepared in a similar manner as described above in 92% yield (FIG. 2I). $^1$H NMR (CDCl$_3$) δ 7.51–7.54 (dd, 1H, ArH), 7.27–7.31 (t, 1H, ArH), 6.98–7.01 (dd, 1H, ArH), 6.86–6.9 (d of t, 1H, ArH), 6.78 (s, 1H, OH), 3.39–3.4 (t, 2H, CH$_2$), 2.11–2.16 (m, 2H, CH$_2$), 1.26–1.46 (m, 4H, CH$_2$), 0.86–0.97 (t, 3H, CH$_3$).

2-Hydroxyphenylhex-2-ynyl sulfide (83) was prepared in a similar manner as described above in 51% yield. $^1$H NMR (CDCl$_3$) δ 7.51–7.54 (dd, 1H, ArH), 7.26–7.32 (t, 1H, ArH), 6.98–7.01 (dd, 1H, ArH), 6.85–6.9 (t, 1H, ArH), 6.78 (s, 1H, OH), 3.39–3.41 (t, 2H, CH$_2$), 2.08–2.15 (m, 2H, CH$_2$), 1.43–1.55 (m, 2H, CH$_2$), 0.89–0.95 (t, 3H, CH$_3$).

2-Hydroxyphenylpent-2-ynyl sulfide (84) was prepared in a similar manner as described above in 59% yield. $^1$H NMR (CDCl$_3$) δ 7.51–7.54 (dd, 1H, ArH), 7.26–7.32 (t, 1H, ArH), 6.98–7.01 (dd, 1H, ArH), 6.85–6.9 (t, 1H, ArH), 6.78 (s, 1H, OH), 3.39–3.41 (t, 2H, CH$_2$), 2.08–2.15 (m, 2H, CH$_2$), 0.89–0.95 (t, 3H, CH$_3$).

2-Hydroxyphenylbut-2-ynyl sulfide (85) was prepared in a similar manner as described above in 61% yield. $^1$H NMR (CDCl$_3$) δ 7.51–7.54 (dd, 1H, ArH), 7.27–7.32 (t, 1H, ArH), 6.98–7.01 (dd, 1H, ArH), 6.86–6.91 (t, 1H, ArH), 6.78 (s, 1H, OH), 3.35–3.38 (q, 2H, CH$_2$), 1.77–1.79 (t, 3H, CH$_3$).

2-Hydroxyphenyl-prop-2-ynyl sulfide (86): was prepared in a similar manner as described above in 58% yield (FIG. 2I). $^1$H NMR (CDCl$_3$) δ 7.54–7.57 (dd, 1H, ArH), 7.29–7.34 (t, 1H, ArH), 7.0–7.02 (dd, 1H, ArH), 6.87–6.92 (t, 1H, ArH), 6.72 (s, 1H, OH), 3.39–3.4 (d, 2H, CH$_2$), 2.25 (s, 1H, CH).

Figure 2H:
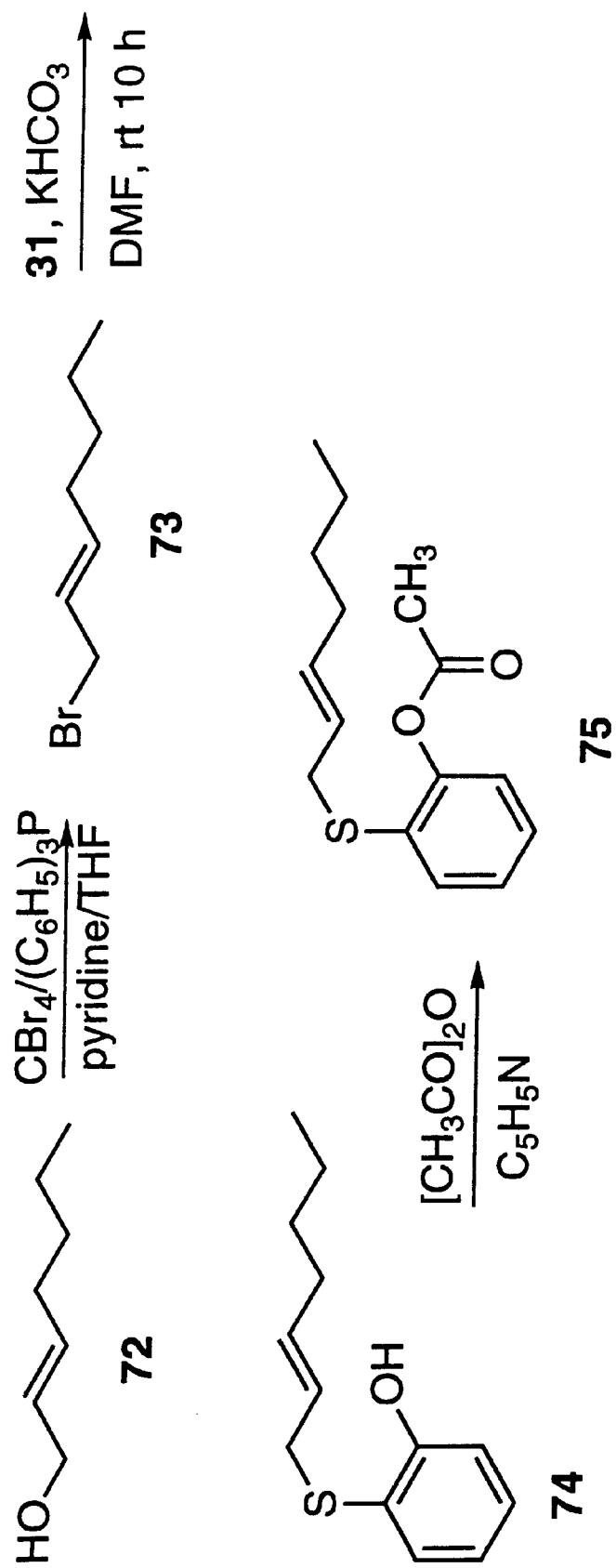
FIG. 2H shows the synthetic scheme for the synthesis of compounds 73, 74 and 75.
Figure 21:
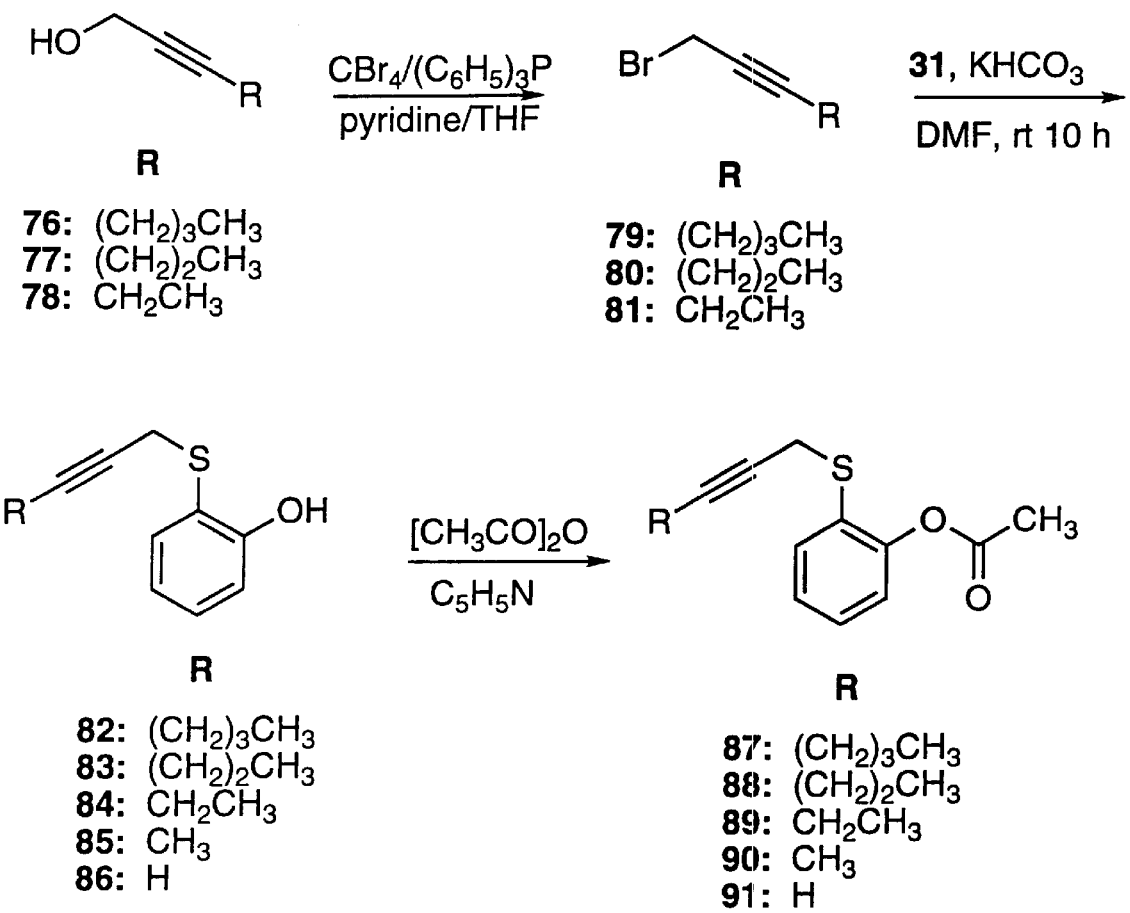
Figure 2J:
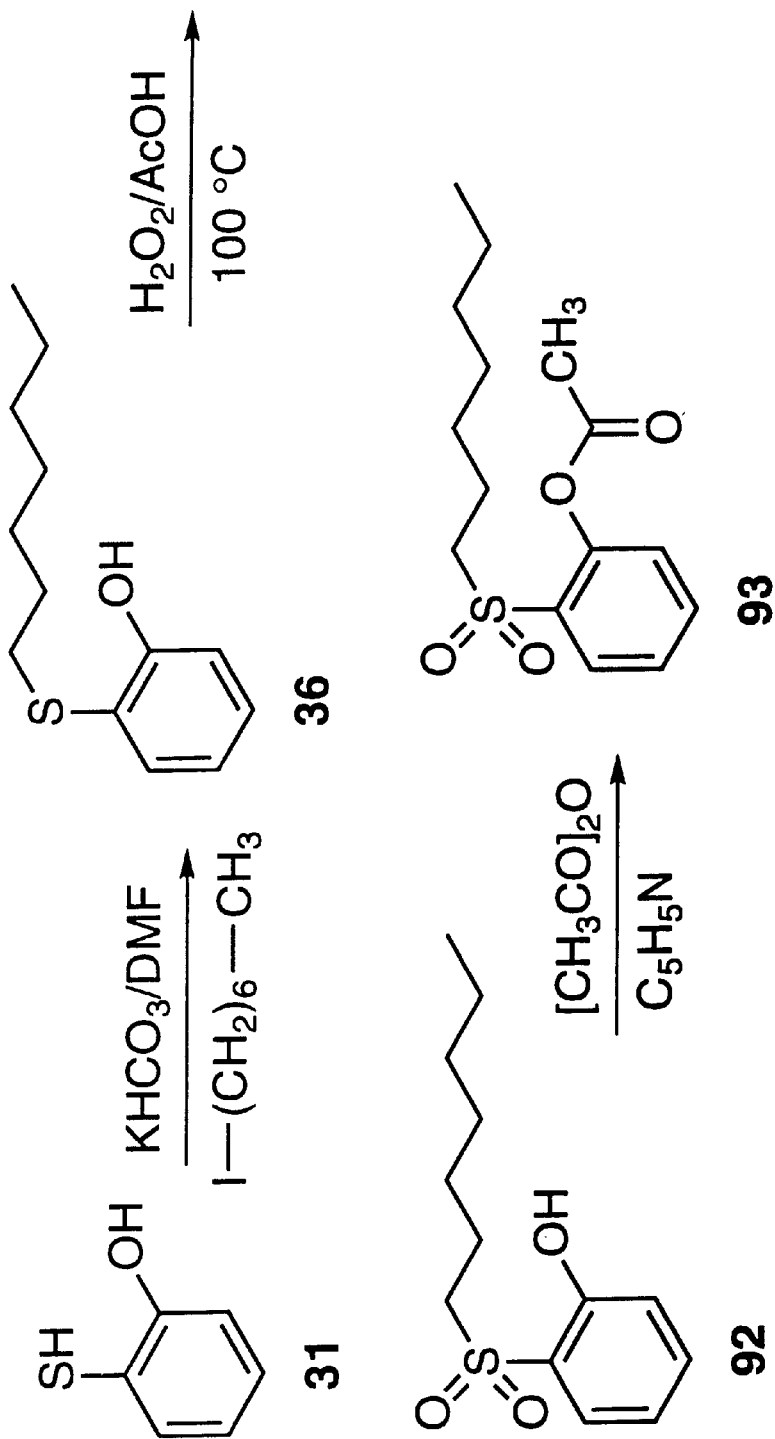
FIG. 2J shows the synthetic scheme for the synthesis of compounds 36, 92, and 93.
Figure 2K:
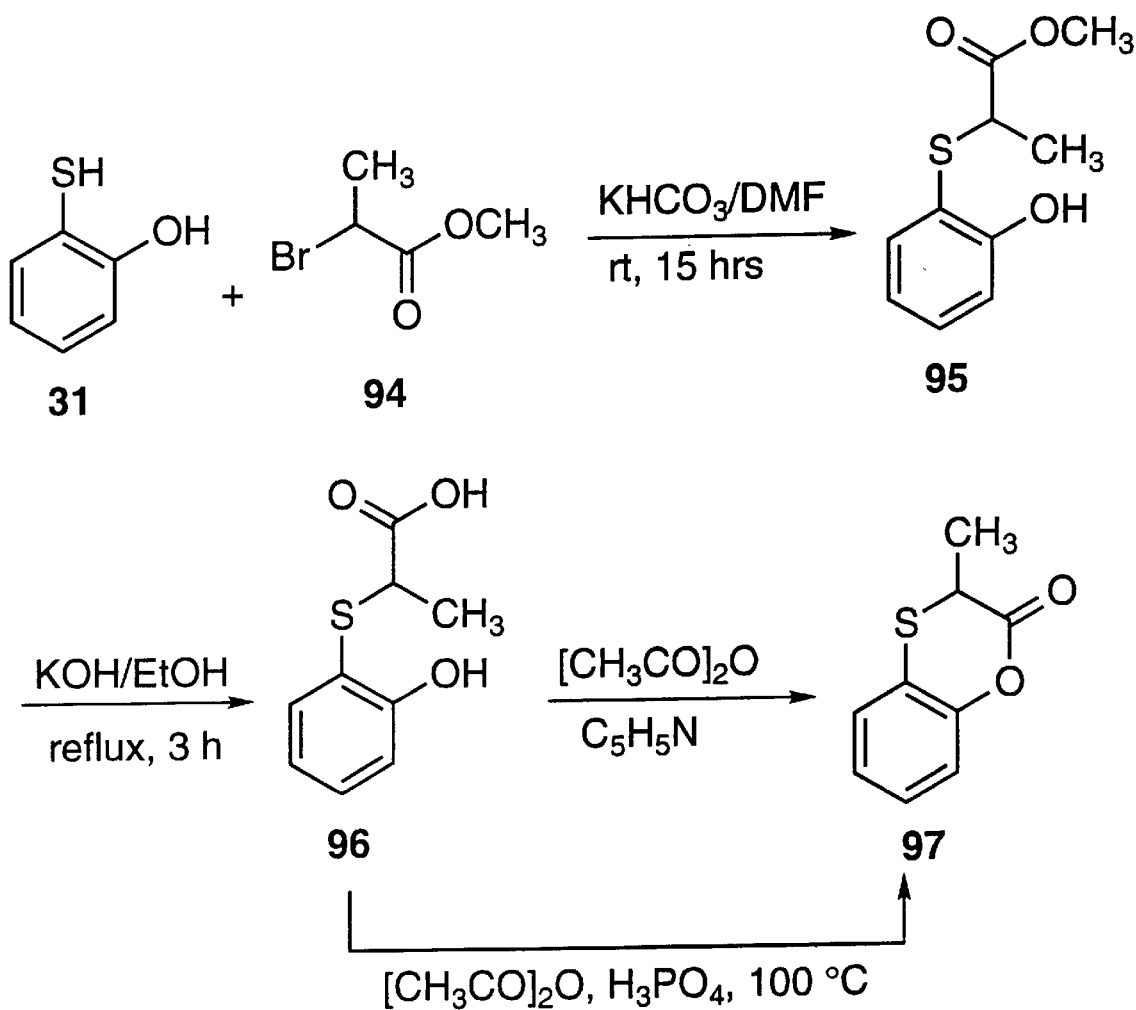
FIG. 2K shows the synthetic scheme for the synthesis of compounds 95, 96 and 97.
Figure 3:
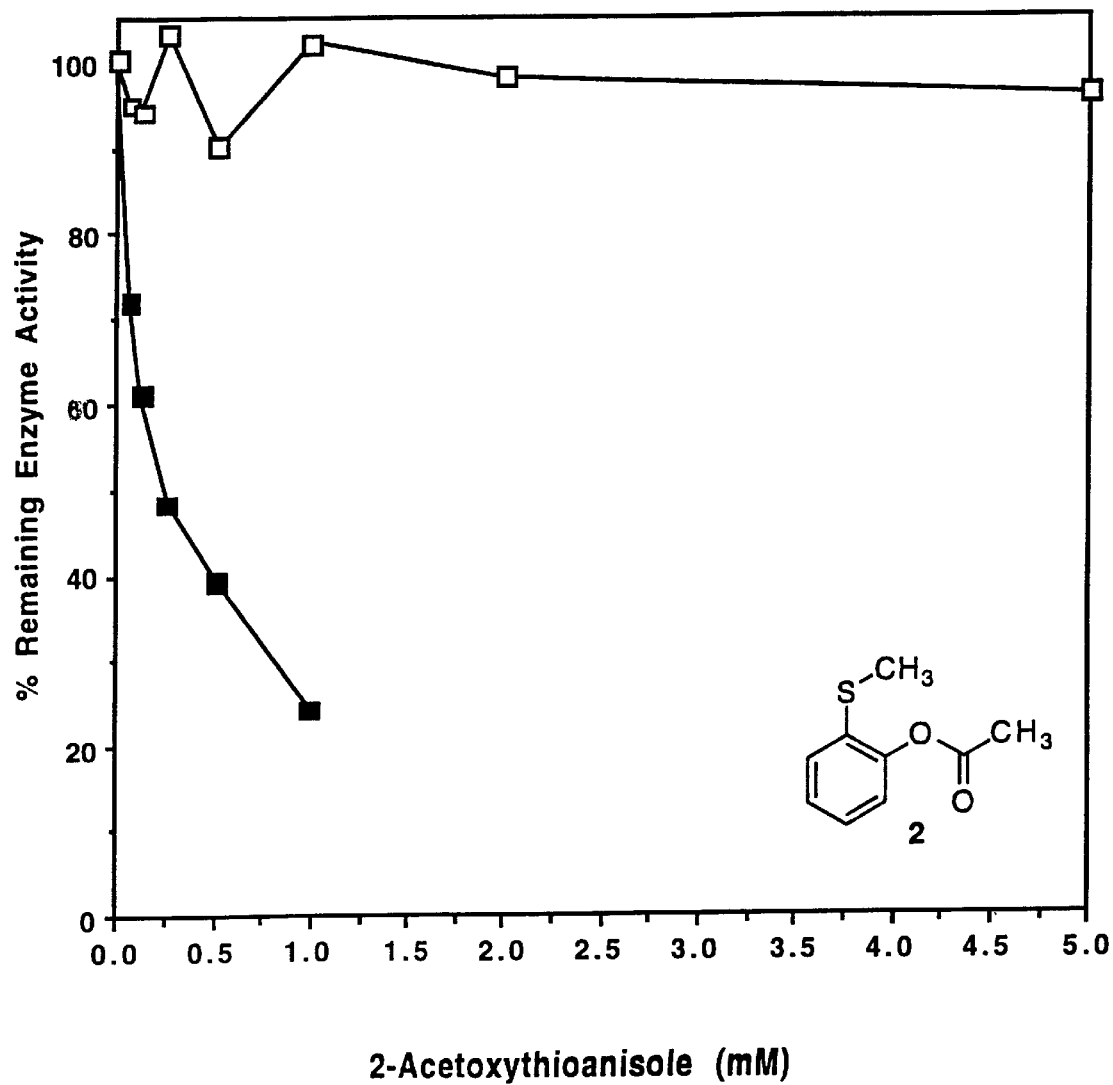
FIG. 3 shows the time- and concentration-dependent inhibition of human PGHS-2 and ovine PGHS-1 by 2-acetoxythioanisole (2). HoloPGHS-1 (22 nM) or holoPGHS-2 (88 nM) was incubated with the indicated concentrations of 2 for 3 hours at room temperature. Cyclooxygenase reaction was initiated by the addition of 50 μM [1-$^{14}$C]—arachidonic acid for 30 sec at 37° C. Closed squares, PGHS-2+2; open squares, PGHS-1+2. 2-Acetoxythioanisole (mM) % Remaining Enzyme.

2-Hydroxythiophenoxy)methylpropionate (95): colorless oil in 67% yield (FIG. 2K). $^1$H NMR (CDCl$_3$) δ 7.42–7.45 (dd, 1H, ArH), 7.25–7.3 (m, 1H, ArH), 7.06 (s, 1H, OH), 6.9–7.0 (dd, 1H, ArH), 6.86–6.89 (m, 1H, ArH), 3.61–3.67 (s and q, 4H, CH$_3$ and CH), 1.45–1.47 (d, 3H, CH$_3$); FAB-MS 213 (MH$^+$, 36), 212 (M$^+$, 90), 181 (30), 153 (100), 79 (100).

2-(2-Hydroxythiophenoxy)propionic acid (96): obtained in a similar manner as a colorless oil in 77% yield (FIG. 2K). $^1$H NMR (CDCl$_3$) δ 7.46–7.49 (dd, 1H, ArH), 7.29–7.34 (m, 1H, ArH), 6.9–7.01 (dd, 1H, ArH), 6.85–6.89 (m, 1H, ArH), 3.59–3.66 (q, 4H, CH), 1.47–1.50 (d, 3H, CH$_3$); FAB-MS 199 (MH$^+$, 20), 198 (M$^+$, 52), 185 (60), 153 (60), 137 (50), 93 (82), 79 (100).

EXAMPLE 25

Procedure For the Acetylation of 2-Hydroxyphenylalkyl sulfides

A reaction mixture containing appropriate arenol (2.8 mmol) in 1 mL of CH$_2$Cl$_2$ was treated with dry pyridine (2.85 mmol) and acetic anhydride (2.85 mmol) and this reaction mixture was allowed to stir at room temperature overnight. The solvent was removed under vacuo and diluted with water. The aqueous solution was extracted with ethyl ether (2×10 mL) and the combined ether extracts were washed with water, dried (MgSO$_4$), filtered, and the solvent removed under reduced pressure. The crude product was purified by column chromatography on silica gel (EtOAc:hexanes; 5:95).

2-Acetoxyphenylethyl sulfide (49) was obtained in 74% yield (FIG. 2F). $^1$H NMR (CDCl$_3$) δ 7.35–7.38 (m, 1H, ArH), 7.19–7.22 (m, 2H, ArH), 7.03–7.06 (m, 1H, ArH), 2.86–2.93 (q, 2H, CH$_2$), 2.34 (s, 3H, CH$_3$), 1.27–1.32 (t, 3H, CH$_3$); FAB-MS 197 (MH$^+$, 65), 196 (M$^+$, 80), 154 (100), 79 (35), 57 (50).

2-Acetoxyphenylpropyl sulfide (50) was obtained in 68% yield (FIG. 2F). $^1$H NMR (CDCl$_3$) δ 7.36–7.39 (m, 1H, ArH), 7.19–7.20 (m, 2H, ArH), 7.03–7.06 (m, 1H, ArH), 2.82–2.87 (t, 2H, CH$_2$), 2.34 (s, 3H, CH$_3$), 1.61–1.69 (q, 2H, CH$_2$), 0.99–1.0 (t, 3H, CH$_3$); FAB-MS 211 (MH$^+$, 45), 210 (M$^+$, 60), 168 (100), 79 (30).

2-Acetoxyphenyl-2-methylpropyl sulfide (51) was obtained in 77% yield (FIG. 2F). $^1$H NMR (CDCl$_3$) δ 7.35–7.38 (m, 1H, ArH), 7.18–7.21 (m, 2H, ArH), 7.02–7.05 (m, 1H, ArH), 2.74–2.76 (d, 2H, CH$_2$), 2.34 (s, 3H, CH$_3$), 1.82–1.86 (m, 1H, CH), 1.01–1.03 (d, 6 H, CH$_3$); FAB-MS 225 (MH$^+$, 70), 224 (M$^+$, 98), 183 (100), 79 (30).

2-Acetoxyphenylpentyl sulfide (52) was obtained in 92% yield (FIG. 2F). $^1$H NMR (CDCl$_3$) δ 7.35–7.38 (m, 1H, ArH), 7.19–7.25 (m, 2H, ArH), 7.02–7.05 (m, 1H, ArH), 2.83–2.88 (t, 2H, CH$_2$), 2.34 (s, 3H, CH$_3$), 1.54–1.65 (m, 2H, CH$_2$), 1.31–1.42 (m, 4H, CH$_2$), 0.86–0.91 (t, 3H, CH$_3$); FAB-MS 239 (MH$^+$, 65), 238 (M$^+$, 90), 197 (100), 196 (82), 79 (35).

2-Acetoxyphenylhexyl sulfide (53) was obtained in 82% yield (FIG. 2F). $^1$H NMR (CDCl$_3$) δ 7.35–7.38 (m, 1H, ArH), 7.18–7.22 (m, 2H, ArH), 7.02–7.06 (m, 1H, ArH), 2.84–2.89 (t, 2H, CH$_2$), 2.34 (s, 3H, CH$_3$), 1.60–1.65 (m, 2H, CH$_2$), 1.39–1.44 (m, 4H, CH$_2$), 1.25–1.29 (m, 4H, CH$_2$), 0.86–0.90 (t, 3H, CH$_3$); FAB-MS 253 (MH$^+$, 44), 252 (M$^+$, 55), 211 (100), 210 (80).

2-Acetoxyphenylheptyl sulfide (54) was obtained in 67% yield (FIG. 2F). $^1$H NMR (CDCl$_3$) δ 7.35–7.38 (m, 1H, ArH), 7.17–7.21 (m, 2H, ArH), 7.02–7.05 (m, 1H, ArH), 2.83–2.88 (t, 2H, CH$_2$), 2.34 (s, 3H, CH$_3$), 1.57–1.67 (m, 2H, CH$_2$), 1.27–1.41 (m, 8H, CH$_2$), 0.85–0.90 (t, 3H, CH$_3$); FAB-MS 267 (MH$^+$, 40), 266 (M$^+$, 55), 225 (100), 224 (84), 79 (32).

2-Acetoxyphenyloctyl sulfide (55) was obtained in 66% yield (FIG. 2F). $^1$H NMR (CDCl$_3$) δ 7.35–7.38 (m, 1H, ArH), 7.19–7.21 (m, 2H, ArH), 7.02–7.18 (m, 1H, ArH), 2.83–2.88 (t, 2H, CH$_2$), 2.34 (s, 3H, CH$_3$), 1.57–1.65 (m, 2H, CH$_2$), 1.38–1.43 (m, 2H, CH$_2$), 1.26–1.38 (m, 8H, CH$_2$), 0.85–0.89 (t, 3H, CH$_3$); FAB-MS 281 (MH$^+$, 32), 280 (M$^+$, 36), 239 (100), 238 (70), 126 (20), 79 (20).

2-Acetoxyphenylnonyl sulfide (56) was obtained in 85% yield (FIG. 2F). $^1$H NMR (CDCl$_3$) δ 7.35–7.37 (m, 1H, ArH), 7.19–7.21 (m, 2H, ArH), 7.03–7.05 (m, 1H, ArH), 2.84–2.88 (t, 2H, CH$_2$), 2.34 (s, 3H, CH$_3$), 1.58–1.64 (m, 2H, CH$_2$), 1.39–1.42 (m, 2H, CH$_2$), 1.26–1.29 (m, 10H, CH$_2$), 0.86–0.89 (t, 3H, CH$_3$); FAB-MS 295 (MH$^+$, 28), 294 (M$^+$, 40), 253 (100), 252 (80), 126 (25), 79 (32).

2-Acetoxyphenylcyclohexyl sulfide (57) was obtained in 78% yield (FIG. 2F). $^1$H NMR (CDCl$_3$) δ 7.45–7.47 (dd, 1H, ArH), 7.23–7.27 (dd, 1H, ArH), 7.17–7.21 (t, 1H, ArH), 7.04–7.07 (dd, 1H, ArH), 3.07–3.08 (m, 1H, CH), 2.34 (s, 3H, CH$_3$), 1.94–1.96 (m, 2H, CH$_2$), 1.75–1.78 (m, 2H, CH$_2$), 1.25–1.62 (m, 6H, CH$_2$); FAB-MS 251 (MH$^+$, 84), 250 (M$^+$, 100), 209 (75), 208 (94), 169 (75), 126 (55), 79 (56).

2-Acetoxyphenylcycloheptyl sulfide (58) was obtained in 64% yield (FIG. 2F). $^1$H NMR (CDCl$_3$) δ 7.41–7.43 (dd, 1H, ArH), 7.17–7.26 (m, 2H, ArH), 7.04–7.06 (dd, 1H, ArH), 3.29–3.34 (m, 1H, CH), 2.34 (s, 3H, CH$_3$), 1.95–2.02 (m, 2H, CH$_2$), 1.69–1.72 (m, 2H, CH$_2$), 1.46–1.71 (m, 8H, CH$_2$); FAB-MS 265 (MH$^+$, 55), 264 (M$^+$, 94), 222 (80), 169 (100), 126 (52), 95 (72), 79 (80).

2-Acetoxyphenylbenzyl sulfide (59) was obtained in 75% yield (FIG. 2F). $^1$H NMR (CDCl$_3$) δ 7.21–7.32 (m, 7H, ArH), 7.13–7.16 (m, 1H, ArH), 7.06–7.07 (m, 1H, ArH), 4.05 (s, 2H, CH$_2$), 2.32 (s, 3H, CH$_3$); FAB-MS 259 (MH$^+$, 52), 258 (M$^+$, 54), 217 (58), 216 (64), 91 (100).

2-Acetoxyphenyl-2-phenylethyl sulfide (60) was obtained in 96% yield (FIG. 2F). $^1$H NMR (CDCl$_3$) δ 7.40–7.43 (dd, 1H, ArH), 7.18–7.31 (m, 7H, ArH), 7.05–7.08 (dd, 1H, ArH), 3.1–3.13 (t, 2H, CH$_2$), 2.87–2.91 (t, 2H, CH$_2$), 2.34 (s, 3H, CH$_3$); FAB-MS 273 (MH$^+$, 44), 272 (M$^+$, 46), 231 (64), 105 (100).

2-Acetoxyphenyl-3-phenylpropyl sulfide (61) was obtained in 66% yield (FIG. 2F). $^1$H NMR (CDCl$_3$) δ 7.15–7.33 (m, 8 H, ArH), 7.03–7.05 (dd, 1H, ArH), 2.84–2.89 (t, 2H, CH$_2$), 2.71–2.76 (t, 2H, CH$_2$), 2.33 (s, 3H, CH$_3$), 1.91–1.96 (m, 2H, CH$_2$); FAB-MS 287 (MH$^+$, 36), 286 (M$^+$, 40), 245 (100), 244 (70), 117 (50), 91 (90).

2-Acetoxyphenyl-3-phenoxypropyl sulfide (62) was obtained in 83% yield (FIG. 2F). $^1$H NMR (CDCl$_3$) δ 7.41–7.43 (dd, 1 H, ArH), 7.18–7.40 (m, 4H, ArH), 7.04–7.06 (dd, 1H, ArH), 6.87–7.03 (m, 3H, ArH), 4.03–4.07 (t, 2H, CH$_2$), 3.06–3.11 (t, 2H, CH$_2$), 2.33 (s, 3H, CH$_3$), 2.05–2.12 (m, 2H, CH$_2$); FAB-MS 303 (MH$^+$, 34), 302 (M$^+$, 34), 260 (68), 209 (50), 167 (100), 133 (50), 107 (30), 79 (40).

2-Acetoxyphenyl-8-carboxyheptyl sulfide (63) was obtained in 47% yield (FIG. 2F). 1H NMR (CDCl$_3$) δ 7.34–7.36 (m, 1 H, ArH), 7.18–7.25 (m, 2H, ArH), 7.04–7.05 (m, 1H, ArH), 2.83–2.88 (t, 2H, CH$_2$), 2.31–2.36 (s merged with a triplet, 5H, SCH$_3$, and CH$_2$), 1.57–1.64 (m, 4H, CH$_2$), 1.31–1.44 (m, 6H, CH$_2$); FAB-MS 311 (MH$^+$, 28), 293 (22), 268 (70), 251 (100), 126 (44), 79 (70).

2-Acetoxyphenyl-2-butoxyethyl sulfide (67) was obtained in 72% yield (FIG. 2G). $^1$H NMR (CDCl$_3$) δ 7.42–7.45 (m, 1H, ArH), 7.20–7.24 (m, 2H, ArH), 7.04–7.19 (m, 1H, ArH), 3.55–3.60 (t, 2H, CH$_2$), 3.40–3.44 (t, 2H, CH$_2$), 3.04–3.08 (t, 2H, CH$_2$), 2.34 (s, 3H, CH$_3$), 1.49–1.56 (m, 2H, CH$_2$), 1.31–1.39 (m, 2H, CH$_2$), 0.88–0.93 (t, 3H, CH$_3$); FAB-MS 269 (MH$^+$, 24), 268 (M$^+$, 40), 226 (44), 195 (100), 125 (24).

2-Acetoxyphenyl-3-ethoxypropyl sulfide (71) was obtained in 70% yield (FIG. 2G). $^1$H NMR (CDCl$_3$) δ 7.39–7.41 (m, 1 H, ArH), 7.19–7.22 (m, 2H, ArH), 7.03–7.06 (m, 1H, ArH), 3.43–3.51 (m, 4H, CH$_2$), 2.96–2.99 (t, 2H, CH$_2$), 2.34 (s, 3H, CH$_3$), 1.86–1.89 (m, 2H, CH$_2$), 1.17–1.21 (t, 3H, CH$_3$); FAB-MS 255 (MH$^+$, 100), 254 (M$^+$, 90), 212 (84), 209 (54), 167 (66), 85 (30).

2-Acetoxyphenyl-trans-hept-2-enyl sulfide (75) was obtained in 62% yield (FIG. 2H). $^1$H NMR (CDCl$_3$) δ 7.36–7.39 (m, 2 H, ArH), 7.15–7.25 (dd, 1H, ArH), 7.03–7.06 (dd, 1H, ArH), 5.41–5.56 (m, 2H, olefinic H), 3.45–3.47 (d, 2H, CH$_2$), 2.34 (s, 3H, CH$_3$), 1.93–2.0 (m, 2H, CH$_2$), 1.2–1.36 (m, 4H, CH2), 0.83–0.94 (t, 3H, CH$_3$).

2-Acetoxyphenyl-hept-2-ynyl sulfide (87) was obtained in 56% yield. $^1$H NMR (CDCl$_3$) δ 7.53–7.56 (dd, 1H, ArH), 7.22–7.27 (m, 2H, ArH), 7.08–7.09 (dd, 1H, ArH), 3.57–3.58 (t, 2H, CH$_2$), 2.34 (s, 3H, CH$_3$), 2.13–2.17 (m, 2H, CH$_2$), 1.32–1.45 (m, 4H, CH2), 0.85–0.89 (t, 3H, CH$_3$).

2-Acetoxyphenylhex-2-ynyl sulfide (88) was obtained in 56% yield. $^1$H NMR (CDCl$_3$) δ 7.53–7.56 (dd, 1H, ArH), 7.22–7.27 (m, 2H, ArH), 7.06–7.09 (dd, 1H, ArH), 3.57–3.59 (t, 2H, CH$_2$), 2.34 (s, 3H, CH$_3$), 2.10–2.16 (m, 2H, CH$_2$), 1.43–1.51 (q, 2H, CH2), 0.89–0.94 (t, 3H, CH$_3$).

2-Acetoxyphenylpent-2-ynyl sulfide (89) was obtained in 63% yield. $^1$H NMR (CDCl$_3$) δ 7.53–7.56 (dd, 1H, ArH), 7.22–7.27 (m, 2H, ArH), 7.06–7.09 (dd, 1H, ArH), 3.57–3.59 (t, 2H, CH$_2$), 2.34 (s, 3H, CH$_3$), 2.10–2.16 (m, 2H, CH$_2$), 0.89–0.94 (t, 3H, CH$_3$).

2-Acetoxyphenyl-but-2-ynyl sulfide (90) was obtained in 78% yield (FIG. 2I). $^1$H NMR (CDCl$_3$) δ 7.52–7.54 (dd, 1H, ArH), 7.2–7.29 (m, 2H, ArH), 7.06–7.09 (dd, 1H, ArH), 3.55–3.56 (d, 2H, CH$_2$), 2.34 (s, 3H, CH$_3$), 1.8 (s, 3H, CH$_3$).

2-Acetoxyphenyl-prop-2-ynyl sulfide (91) was obtained in 58% yield (FIG. 2I). $^1$H NMR (CDCl$_3$) δ 7.56–7.59 (dd, 1H, ArH), 7.22–7.33 (m, 2H, ArH), 7.08–7.11 (dd, 1H, ArH), 3.56–3.57 (d, 2H, CH$_2$), 2.35 (s, 3H, CH$_3$), 2.22–2.24 (t, 1H, CH).

EXAMPLE 26

Compound 97

$^1$H NMR spectrum and FAB-MS of the oil obtained following chromatography indicated acetylation had not taken place, instead cyclization had occurred to afford compound 85 in 81% yield.

$^1$H NMR (CDCl$_3$) d 7.22–7.33 (m, 2H, ArH), 7.07–7.12 (m, 2H, ArH), 3.5–3.57 (q, 1H, CH), 1.52–1.59 (d, 3H, CH$_3$); FAB-MS 181 (MH$^+$, 20), 180 (M$^+$, 22), 157 (28), 132 (20), 79 (100).

EXAMPLE 27

Enzymology

Sheep seminal vesicles were purchased from Oxford Biomedical Research, Inc. (Oxford, Mich.). Arachdonic acid was purchased from Nu Chek Prep (Elysian, Minn.). Hematin, hydrogen peroxide, and guaiacol were purchased from Sigma Chemical Co. (St. Louis, Mo.). PGHS-1 was purified from sheep seminal vesicles as described earlier. The specific activity of the protein was 20.9 (μMO2/min)/mg, and the percentage of holoenzyme was 13.5%. Apo-PGHS was prepared as described earlier. Apoenzyme was reconstituted by the addition of hematin to the assay mixtures. Human PGHS-2 (1.62 μg/μl) was obtained from J. Gierse, Monsanto (St. Louis, Mo.).

EXAMPLE 28

Cyclooxygenase Activity

Oxygen consumption was measured at 37° C. with a Gilson model ⅚ oxygraph (Gilson Medical Electronics, Inc., Middleton, Wis.) equipped with a clark electrode and a thermostated cuvette. Enzyme aliquots (0.16 μM) were added to 100 mM Tris-HCl at pH 8.0 containing 500 μM phenol and 1 μM hematin in a final volume of 1.3 mL. Oxygen uptake was initiated by the addition of 100 μM sodium arachidonate, and the initial reaction velocity was determined from the linear portion of the oxygen uptake curve.

EXAMPLE 29

Peroxidase Activity

Assays were performed at 25° C. on a Shimadzu UV 160U by measuring the initial rates of oxidation of guaiacol at 436 nm. Enzyme aliquots (0.16 μM) were added to 100 mM Tris-HCl (pH 8) containing 1 μM heme and 500 μM guaicol in 1 mL disposable cuvettes. Reaction was initiated by the addition of 400 μM hydrogen peroxide.

Figure 4:
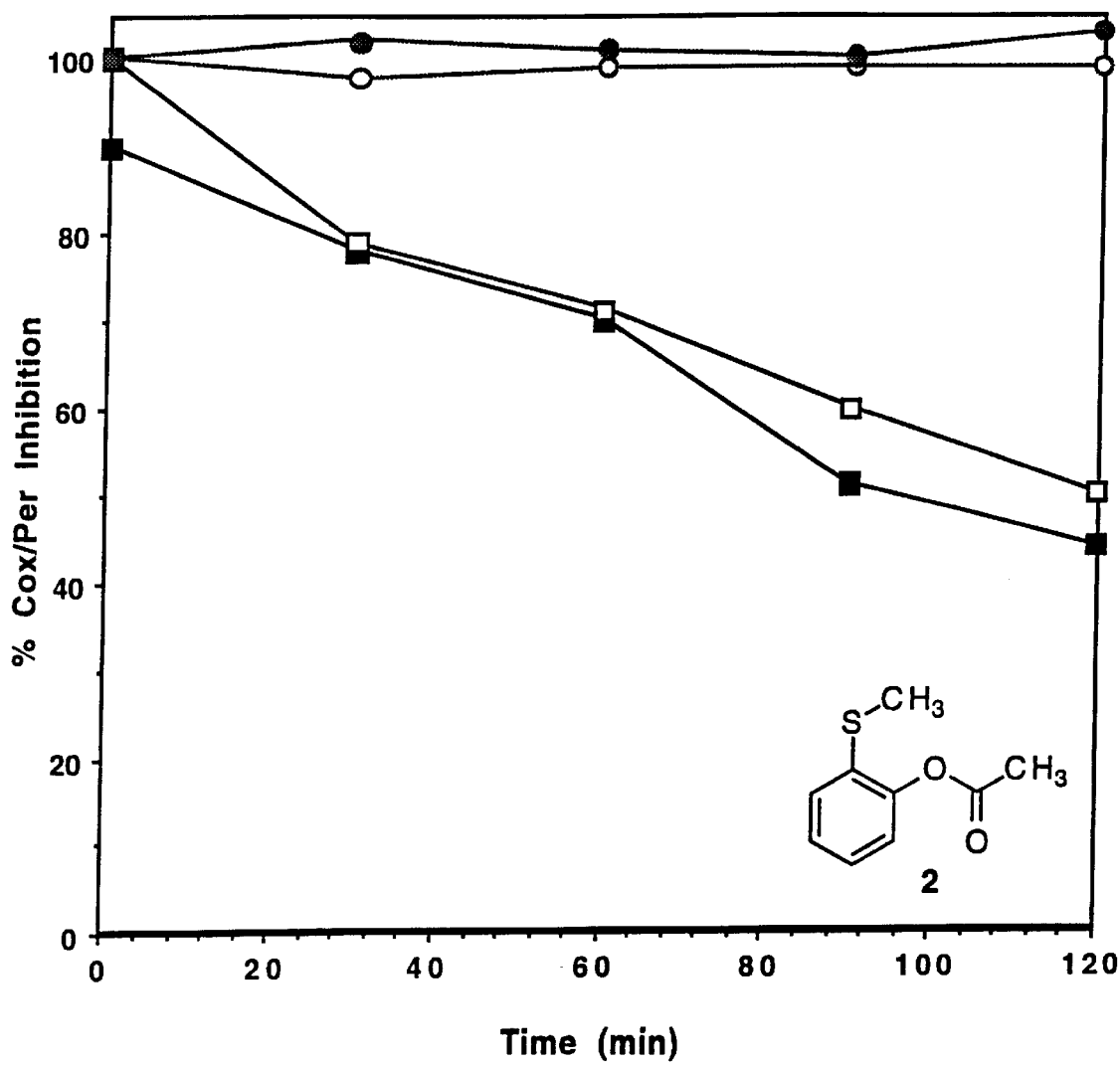
FIG. 4 shows the time-dependent inhibition of the cyclooxygenase activity of Apo and HoloPGHS-2 by 2-Acetoxythioanisole (2). ApoPGHS-2 (5 μM) or holoPGHS-2 (5 μM) was incubated with a 1000-fold excess of 2. Periodic 0.16 μM enzyme aliquots (final inhibitor concentration ~160 μM) were analyzed for remaining cyclooxygenase or peroxidase activity as described above. Closed squares, cyclooxygenase activity of holoPGHS-2; open squares, cyclooxygenase activity of apoPGHS-2; closed circles, peroxidase activity of holoPGHS-2; open circles, peroxidase activity of apoPGHS-2.

EXAMPLE 30
Time-Dependent Inhibition of the Cyclooxygenase and Peroxidase Activity of Apo and HoloPGHS-1 and PGHS-2 Using the Oxygen Uptake Assay ApoPGHS-1 (2.48 μg/μl) (5 μM) or apoPGHS-2 (1.62 μg/μl) (5 μM) in 100 mM Tris buffer, pH 8.0 containing 500 μM phenol was treated with inhibitor and incubated at room temperature (FIG. 4). Periodically, 0.16 μM apoPGHS-1 or apoPGHS-2 aliquots were analyzed for remaining cyclooxygenase activity or peroxidase activity as described. In a similar fashion apoPGHS-1 or apoPGHS-2 (5 μM) in 100 mM Tris buffer, pH 8.0 containing 500 μM phenol was treated with 2 equivalents of hematin (500 μM stock solution in DMSO) and then treated with inhibitor and incubated at room temperature. Periodically, 0.16 μM apoPGHS-1 or apoPGHS-2 aliquots were analyzed for remaining cyclooxygenase activity or peroxidase activity (FIG. 4).

Figure 5:
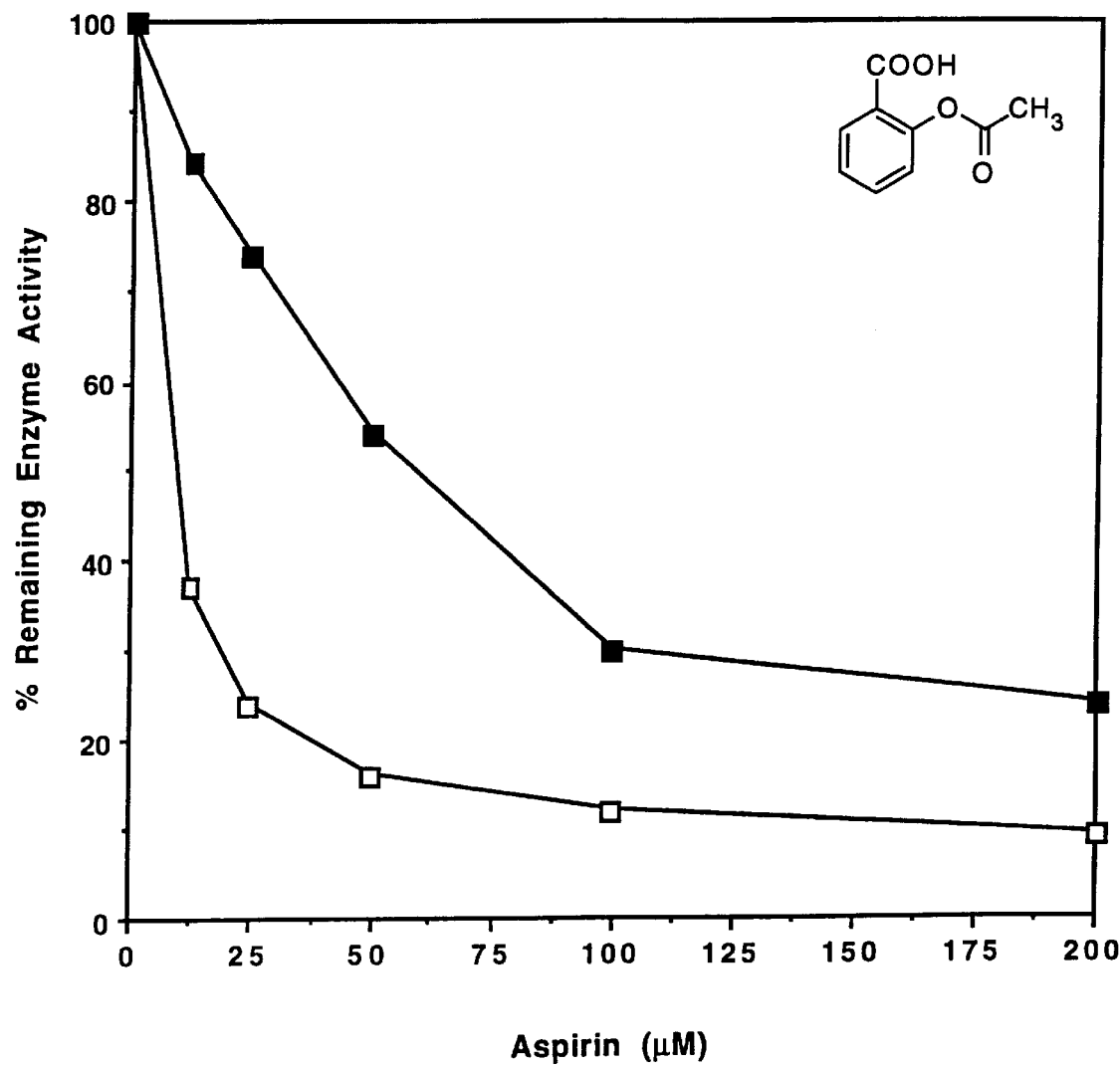
FIG. 5 shows the time- and concentration-dependent inhibition of human PGHS-2 and ovine PGHS-1 by aspirin. HoloPGHS-1 (22 nM) or holoPGHS-2 (88 nM) was incubated with the indicated concentrations of aspirin for 1 hour at room temperature. Cyclooxygenase activity was initiated by the addition of [1-$^{14}$C]-arachidonic acid (50 μM) for 30 sec at 37° C. Open squares, PGHS-1+aspirin; closed squares, PGHS-2+aspirin.
Figure 7:
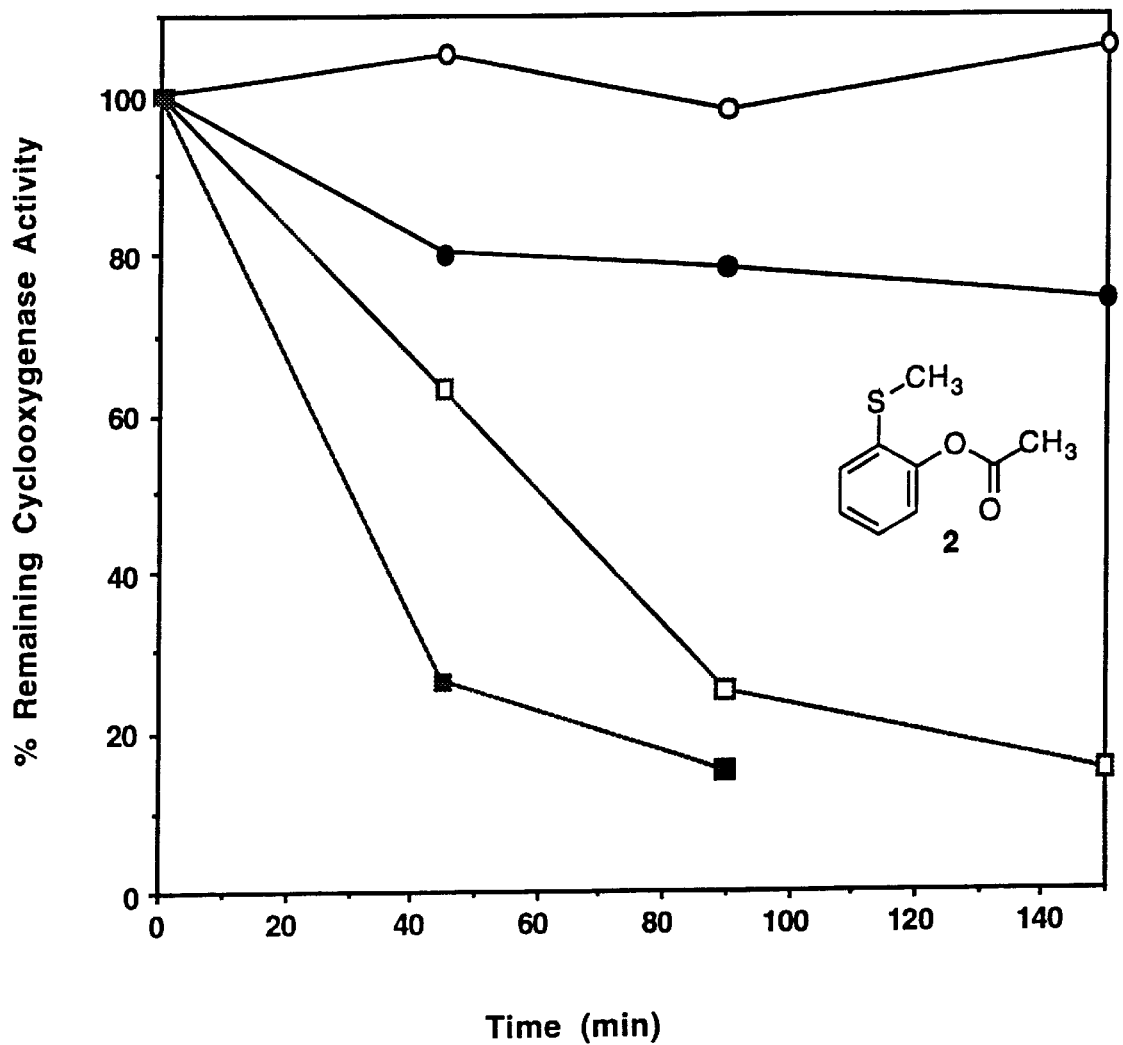
FIG. 7 shows the effect of pH on the inhibition of the cyclooxygenase activity of human PGHS-2 by 2-acetoxythioanisole (2). ApoPGHS-2 (5 μM, 1.62 μg/μL) in 100 mM sodium phosphate buffer of pH 6, 7, 8, and 9 was reconstituted with 2 equivalents of hematin. Compound 2 (1000-fold excess) in DMSO was added to the reaction mixture. Periodically, 0.16 μM enzyme aliquots (final inhibitor concentration ~178 μM) were analyzed for remaining cyclooxygenase activity. Open circles, cyclooxygenase activity of holoPGHS-2 treated with 2 at pH 6; closed circles, cyclooxygenase activity of holoPGHS-2+2 at pH 7; open squares, cyclooxygenase activity of holoPGHS-2+2 at pH 8; closed squares, cyclooxygenase activity of holoPGHS-2+2 at pH 9. Control experiments in the absence of inhibitor remained linear throughout the entire assay period.

EXAMPLE 31
Dependence of pH on the Time-Dependent Inhibition of the Cyclooxygenase Activity of HoloPGHS-2 by 2-Acetoxythioanisole (2) and 2-Acetoxyphenylheptyl sulfide (54) Using the Oxygen Uptake Assay: Comparison With Aspirin ApoPGHS-2 (1.62 μg/μl) (5 μM) in 100 mM sodium phosphate buffer, at pH 6, 7, 8, and 9 containing 500 μM phenol was treated with inhibitor (2-acetoxythioanisole 10 mM; 2-acetoxyphenylheptylsulfide 181 μM, or aspirin 32 μM) and incubated at room temperature. Periodically, 0.16 μM apoPGHS-1 or apoPGHS-2 aliquots were analyzed for remaining cyclooxygenase activity or peroxidase activity as described. FIG. 5 shows that aspirin had a greater inhibitory effect on PGHS-1 than PGHS-2. FIG. 7 shows that 2-acetoxythioanisole greatly inhibited cyclooxygenase activity of holoPGHS-2 at pH 9.

Figure 8:
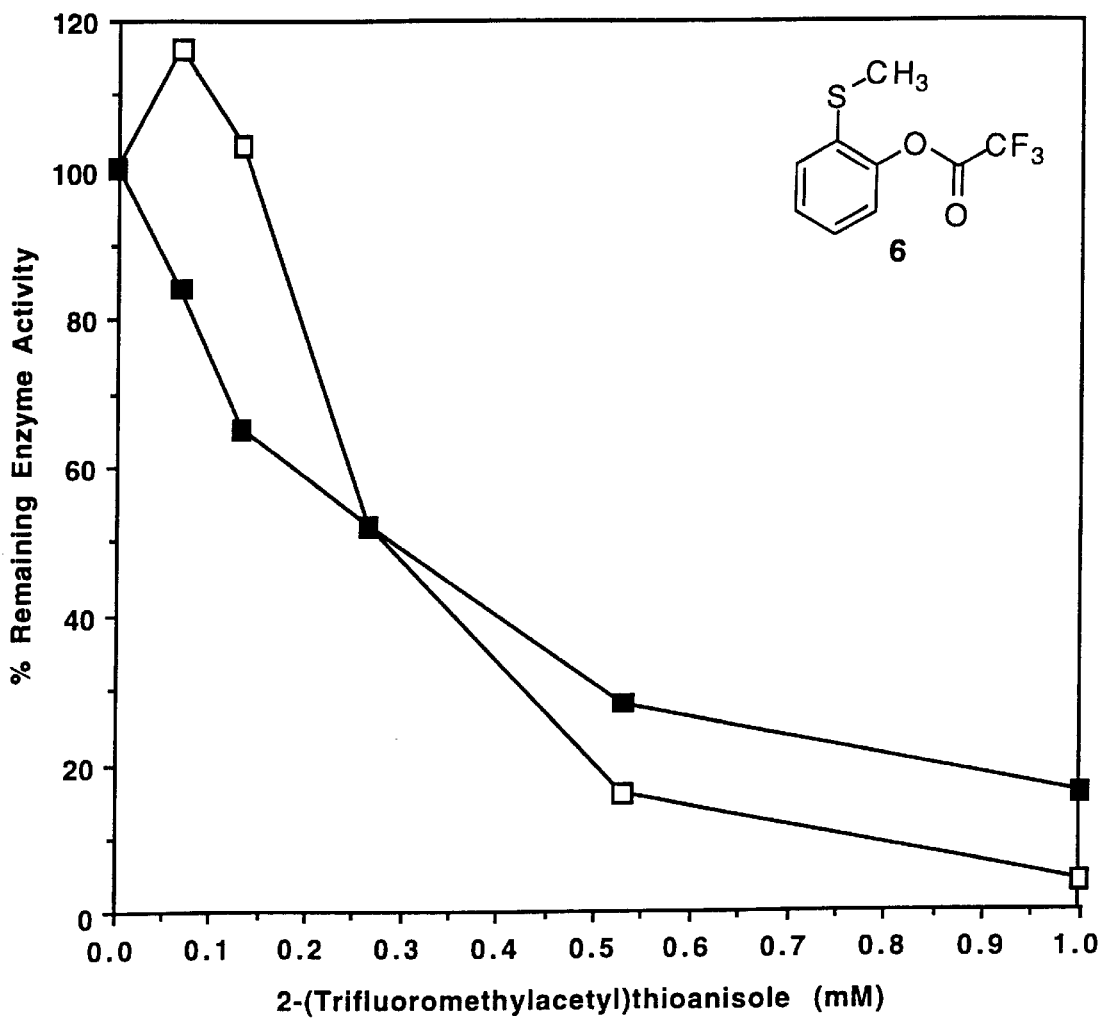
FIG. 8 shows the time- and concentration-dependent inhibition of human PGHS-2 and ovine PGHS-1 by 2-(Trifluoromethylacetoxy)thioanisole (6). HoloPGHS-1 (22 nM) or holoPGHS-2 (88 nM) was incubated with the indicated concentrations of 6 for 3 hours at room temperature. Cyclooxygenase reaction was initiated by the addition of [1-$^{14}$C]-arachidonic acid (50 μM) for 30 sec at 37° C. Open squares, PGHS-1+6; closed squares, PGHS-2+6.

EXAMPLE 32
Time- and Concentration-Dependent Inhibition of Ovine PGHS-1 and human PGHS-2 Using the Thin Layer Chromatography (TLC) Assay Cyclooxygenase activity of ovine PGHS-1 (22 nM) or human PGHS-2 (88 nM) was assayed by TLC. Reaction mixtures of 200 μL consisted of hematin-reconstituted protein in 100 mM Tris-HCl, pH 8.0, 500 μM phenol, and [1-$^{14}$C]arachidonic acid (50 μM, 57 mCi/mmol). For the time-dependent inhibition assay, hematin-reconstituted PGHS-1 (22 nM) or PGHS-2 (88 nM) was preincubated at room temperature for 2 hours and then at 0° C. for 1 hour with varying concentrations of inhibitor in DMSO followed by the addition of [1-$^{14}$C]arachidonic acid (50 μM) for 30 seconds at 37° C. Reactions were terminated by solvent extraction in diethyl ether/methanol/1 M citrate, pH 4.0 (30:4:1). The organic phase was spotted on a TLC plate (Amersham Corp.). The plate was developed with ethyl acetate/methylene chloride/glacial acetic acid (75:25:1) at 4° C. Radiolabeled products were quantitated with a radioactivity scanner (Bioscan, Inc., Washington, D.C.). The conversion of arachidonic acid to products was linear with respect to both protein content and incubation time. The percentage of total products observed at different inhibitor concentrations was divided by the percentage of total products observed for protein samples preincubated for the same time with DMSO. FIG. 8 shows that 0.1 mM of compound 6 inhibited about 35% of human PGHS-2.

Figure 6:
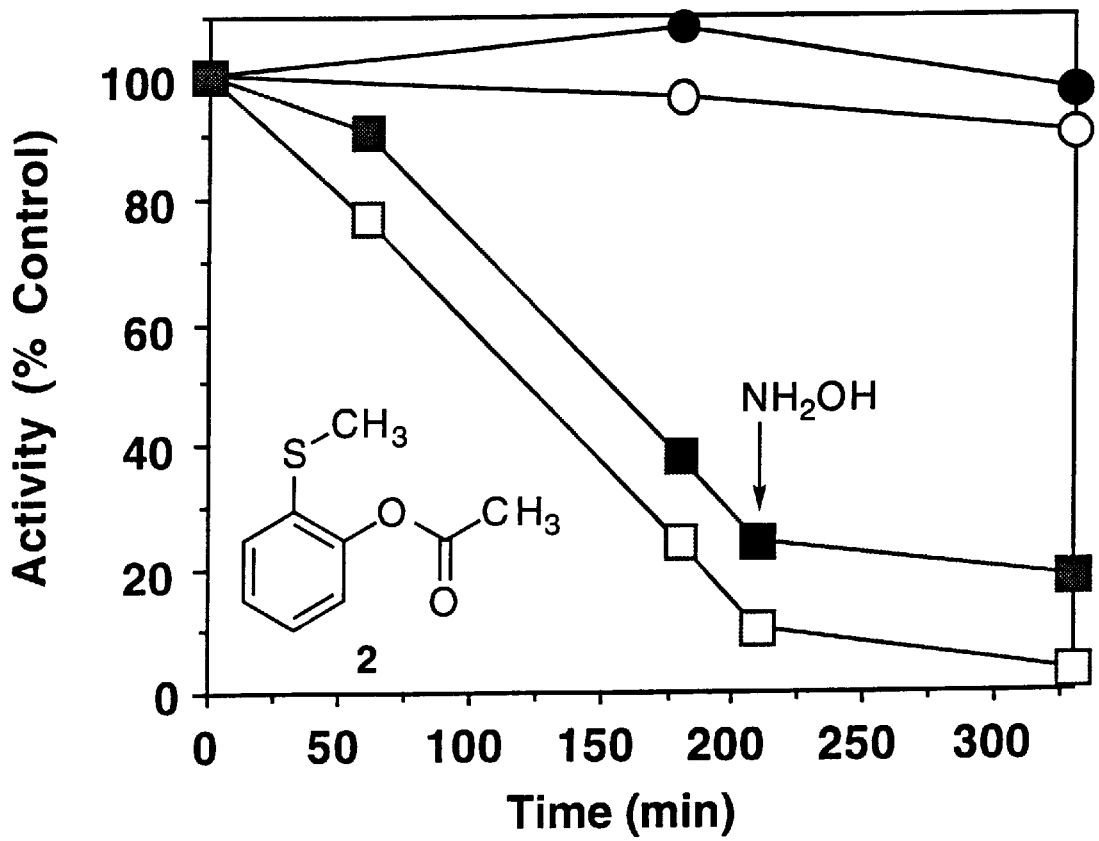
FIG. 6 shows the inactivation of the cyclooxygenase activities of holo and apoPGHS-2 by 2-acetoxythioanisole (2). Apo or HoloPGHS-2 (5 mM) was inactivated with a 1000-fold excess of 2-acetoxythioanisole (2) at 22.5° C. in 100 mM Tris-HCl buffer, pH 8 containing 500 mM phenol for the indicated time period, and then hydroxyl amine (80 mM) in 10 mM Tris-HCl buffer, pH 7.5 was added as indicated by the arrow. Periodic 0.16 μM aliquots of holoPGHS-2 (open circles), holoPGHS-2+2-acetoxythioanisole (open squares), apoPGHS-2 (closed circles), apoPGHS-2+2-acetoxythioanisole (closed squares) were analyzed for remaining cyclooxygenase activity.

EXAMPLE 33
Inactivation of the Cyclooxygenase Activity of Apo- and HoloPGHS-2 by 2-Acetoxy-1-thioanisole and Reactivation by Hydroxylamine ApoPGHS-2 (5 μM) or apoPGHS-2 (5 μM), reconstituted with 2 equivalents of hematin in 100 mM Tris-HCl, pH 8 at 37° C. containing 500 μM phenol was treated with 2-acetoxy-1-thioanisole (10 mM). Periodically, 0.16 μM enzyme aliquots were analyzed for remaining cyclooxygenase activity as described earlier. The cyclooxygenase activity was inhibited by greater than 70% in 2.5 hours. Hydroxylamine hydrochloride (80 mM) in 10 mM Tris-HCl, pH 7.5 was then added to the incubation mixture and 0.16 μM enzyme aliquots were analyzed for reactivation of the inhibited cyclooxygenase-2. A similar reactivation experiment was performed with N-acetylimidazole which inhibits the cyclooxygenase activity of apoPGHS-1 and following addition of hydroxyl amine, the enzyme activity is regenerated. (FIG. 6).

EXAMPLE 34
Synthesis of 2-[1-$^{14}$C]-acetoxythioanisole ($^{14}$C-2)

A reaction mixture containing 2-hydroxythioanisole (1, 3 mg, 21 μmol) in 300 μL of CH$_2$Cl$_2$ was treated with dry pyridine (2.85 μL, 36 μmol) and allowed to stir at room temperature for 5 minutes. CH$_2$Cl$_2$ (200 μL each) was added to the vials containing [1-$^{14}$C]-acetic anhdyride (3 μL of total radiolabeled substance in two vials) (3 μL, 31 μmol, 55 mCi/mmol) and this mixture was transferred via a syringe to the reaction mixture. The vials containing the radiolabeled material were washed with an additional 200 μL of CH$_2$Cl$_2$ and these washings were transferred to the reaction mixture as well. The reaction mixture was stirred overnight at room temperature. The reaction mixture was then loaded on a silica gel column and eluted with EtOAc:hexanes (1:99). At this solvent polarity, unreacted starting material eluted out. The polarity of the solvent was then increased (EtOAc:hexanes; 3:97) and the more polar radiolabeled 2-acetoxythioanisole eluted out (1 mg, 35% yield based on starting 2-hydroxythioanisole). TLC (EtOAc:hexanes; 10:90) single spot ($R_f$=0.625); specific activity 55 mCi/mmol.

EXAMPLE 35
Synthesis of 2-[1-$^{14}$C]-acetoxyphenylhept-2-ynyl sulfide ($^{14}$C-87)

A reaction mixture containing 2-hydroxyphenyl hept-2-ynyl sulfide (82, 4 mg, 18 μmol) in 300 μL of CH$_2$Cl$_2$ was treated with dry pyridine (2.4 μL, 30 μmol) and allowed to stir at room temperature for 5 min. CH$_2$Cl$_2$ (200 μL×2) was added to the vial containing [1-$^{14}$C]-acetic anhdyride (3 μL, 31 μmol, 55 mCi/mmol) and this mixture was transferred via a syringe to the reaction mixture. The reaction mixture was stirred overnight at room temperature. The reaction mixture was then loaded on a silica gel column and eluted with EtOAc:hexanes (2:98) to afford $^{14}$C-79. (1 mg, 10% yield based on starting phenol). TLC (EtOAc:hexanes; 10:90) single spot ($R_f$=0.6); specific activity 55 mCi/mmol.

EXAMPLE 36
Inhibition of Activated RAW264.7 Cells by 2-Acetoxy-1-thioanisole, 2-Acetoxyphenylheptyl sulfide, and Aspirin The murine macrophage cell line RAW264.7 were seeded overnight for 30% confluency the following morning. Overnight DMEM and fetal bovine serum (FBS) was removed and 2 mL DMEM containing 1.5% FBS ±500 ng/mL LPS and 10 units/mL interferon-γ were added for 7.5 hours at 37° C. Activation medium was removed and 2.0 mL SF-DMEM and/or aspirin or 2-acetoxyphenylheptyl sulfide (54) at varying concentrations were added for 30 min at 37° C. Arachidonic acid metabolism was measured by adding 20 μM 14C-AA for 15 min at room temperature. Aliquots (200 μL) were removed into termination solution and run on TLC plates. In the case of 2-acetoxythioanisole (2), following 8 hours of activation, 500 μM 2 was added for the next 3.5 hours. After 11.5 hours of activation, 20 μM [1-$^{14}$C] arachidonic acid was incubated with the cells for 20 minutes at room temperature, and total products were determined by TLC.

Figure 9:
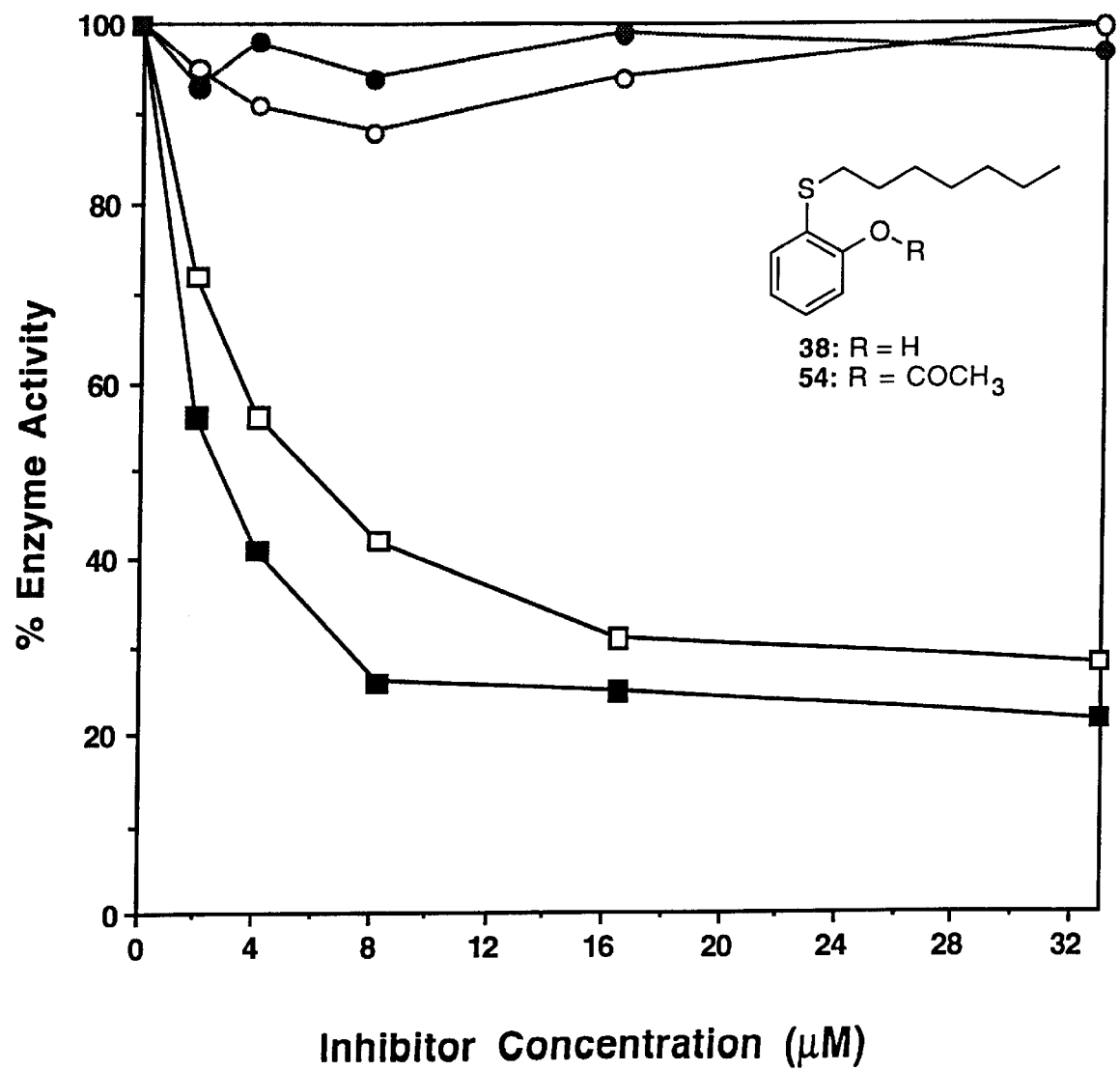
FIG. 9 shows the time- and concentration-dependent inhibition of human PGHS-2 and ovine PGHS-1 by 2-acetoxyphenyl heptyl sulfide (54) and a comparison with 2-Hydroxyphenylheptyl sulfide (38). HoloPGHS-1 (22 nM) or holoPGHS-2 (88 nM) was incubated with the indicated concentrations of 54 and 38 for 3 hours at room temperature. Cyclooxygenase reaction was initiated by the addition of [1-$^{14}$C]-arachidonic acid (50 μM) for 30 seconds at 37° C. Closed squares, cyclooxygenase activity of holoPGHS-2 treated with 54; open squares, cyclooxygenase activity of holoPGHS-1 treated with 54; closed circles, cyclooxygenase activity of holoPGHS-2 treated with 38; open circles, cyclooxygenase activity of holoPGHS-1 treated with 38.
Figure 10:
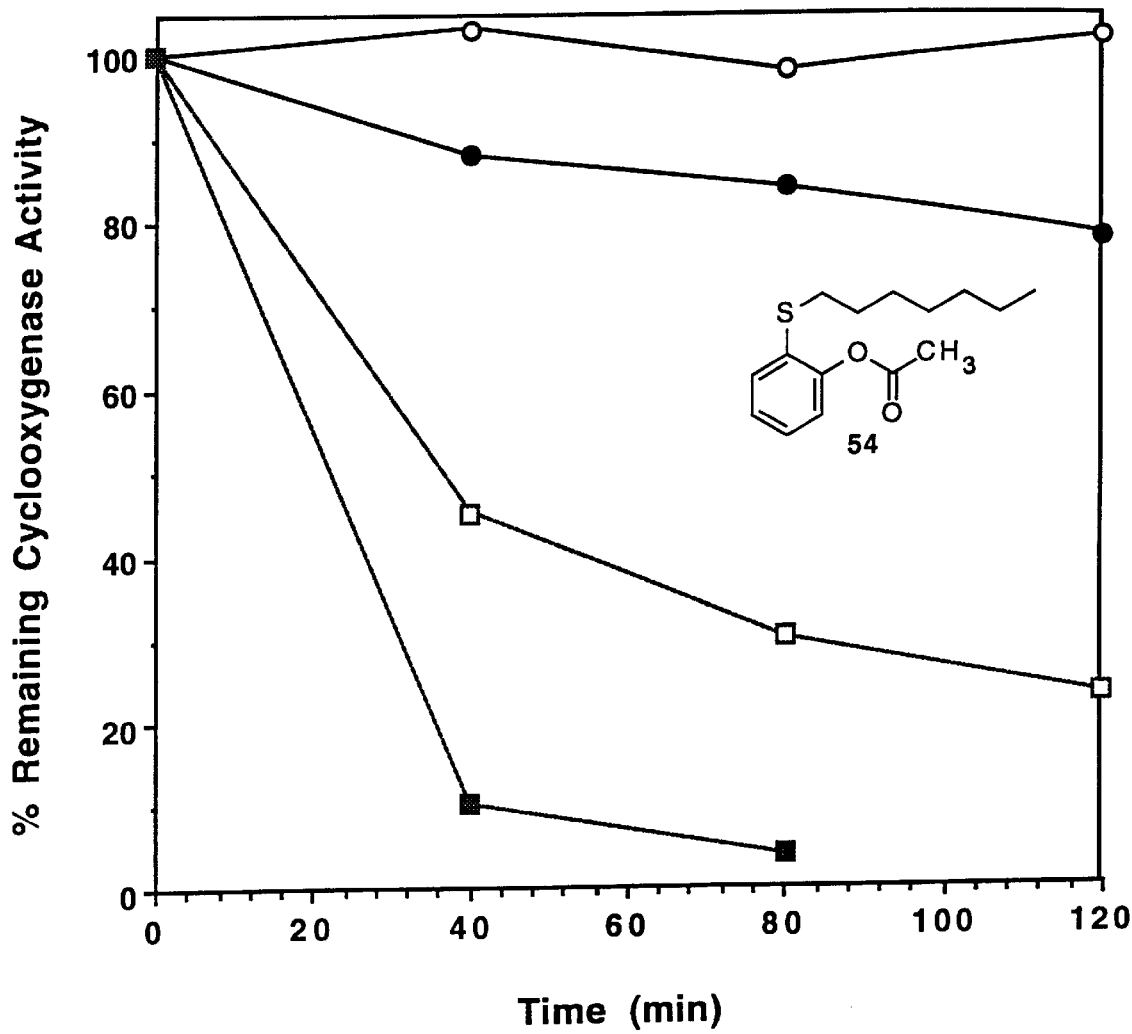
FIG. 10 shows the effect of pH on the inhibition of the cyclooxygenase activity of human PGHS-2 by 2-Acetoxyphenylheptyl sulfide (54). ApoPGHS-2 (5 μM, 1.62 μg/μL) in 100 mM sodium phosphate buffer of pH 6, 7, 8, and 9 was reconstituted with 2 equivalents of hematin. Compound 54 (181 μM) in DMSO was added to the reaction mixture. Periodically, 0.16 μM enzyme aliquots (final inhibitor concentration ~6 μM) were analyzed for remaining cyclooxygenase activity. Open circles, cyclooxygenase activity of holoPGHS-2 treated with 54 at pH 6; closed circles, cyclooxygenase activity of holoPGHS-2+54 at pH 7; open squares, cyclooxygenase activity of holoPGHS-2+54 at pH 8; closed squares, cyclooxygenase activity of holoPGHS-2+54 at pH 9. Control experiments in the absence of inhibitor remained linear throughout the entire assay period.
Figure 11:
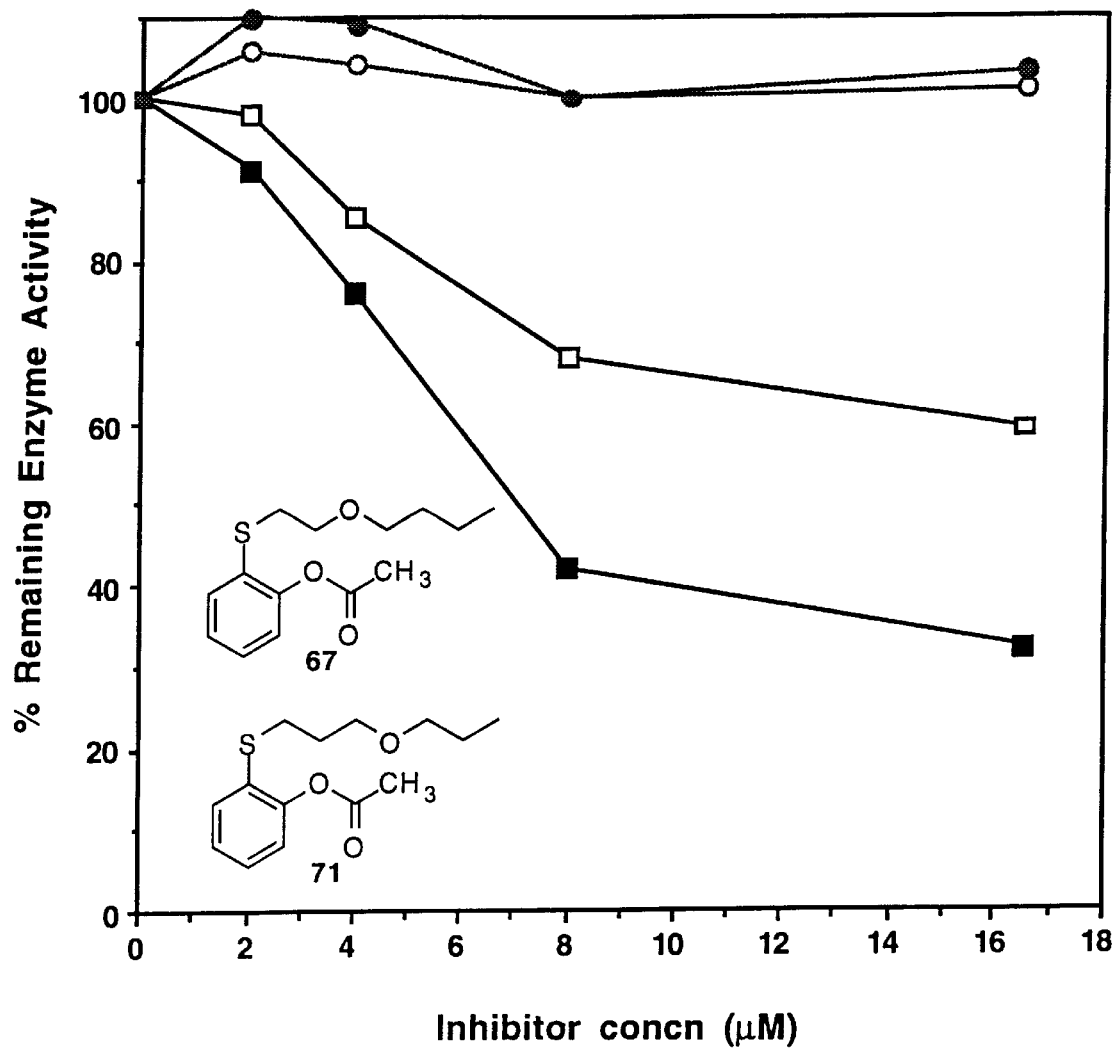
FIG. 11 shows the time-dependency and concentration-dependent inhibition of human PGHS-2 and ovine PGHS-1 by 2-Acetoxyphenyl-2-butoxyethyl sulfide (67) and 2-acetoxyphenyl-3-propionoxypropyl sulfide (71). HoloPGHS-2 (22 nM) or holoPGHS-1 (88 nM) was incubated with the indicated concentrations of 67 or 71 for 3 hours at room temperature. Cyclooxygenase reaction was initiated by the addition of [1-$^{14}$C]-arachidonic acid (50 μM) for 30 sec at 37° C. Closed squares, cyclooxygenase activity of holoPGHS-2 treated with 67; open squares, cyclooxygenase activity of holoPGHS-1 treated with 67; open circles, cyclooxygenase activity of holoPGHS-1 treated with 71; closed circles, cyclooxygenase activity of holoPGHS-2 treated with 71.
Figure 12:
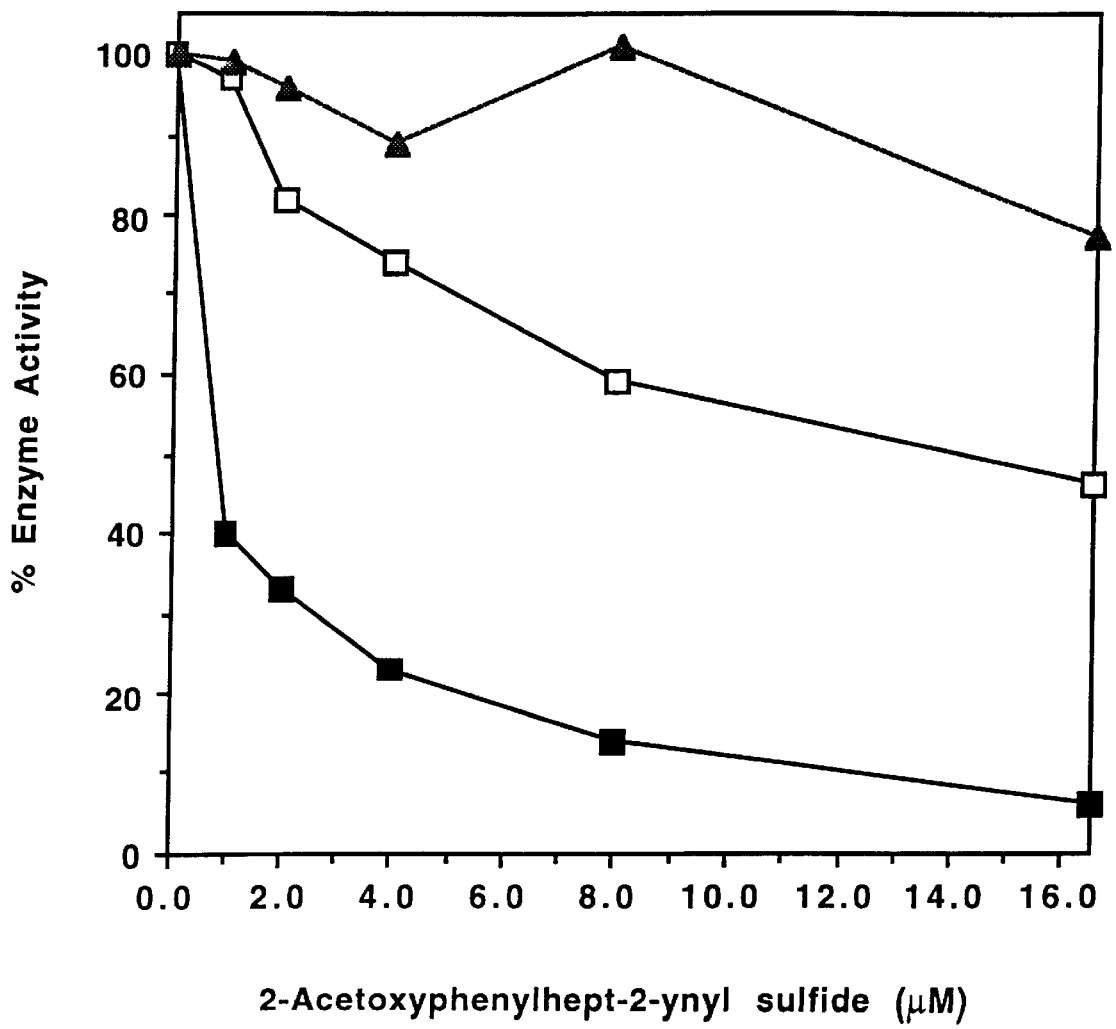
FIG. 12 shows the time- and concentration-dependent inhibition of human PGHS-2 and ovine PGHS-1 by 2-Acetoxyphenyl-hept-2-ynyl sulfide (87). HoloPGHS-1 (22 nM) or holoPGHS-2 (88 nM) was incubated with the indicated concentrations of 87 for 3 hours at room temperature. Cyclooxygenase activity was initiated by the addition of 50 μM [1–14C]-arachidonic acid for 30 sec at 37° C. Closed squares, cyclooxygenase activity of PGHS-2; open squares, cyclooxygenase activity of PGHS-1; closed triangles, cyclooxygenase activity of holoPGHS-2 treated with the corresponding 2-hydroxyphenyl-hept-2-ynyl sulfide (82).
Figure 13:
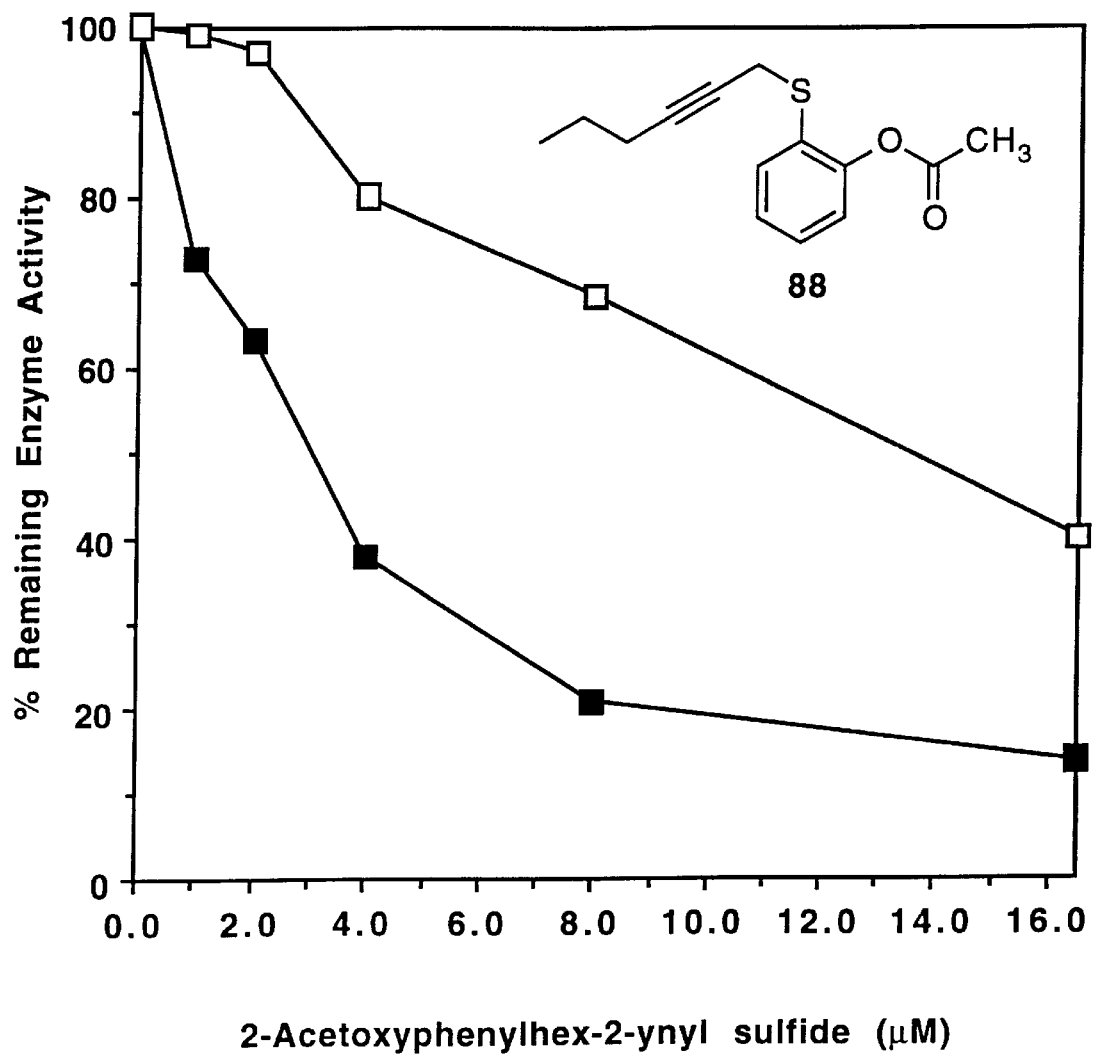
FIG. 13 shows the time and concentration-dependent inhibition of human cyclooxygenase-2 and ovine cyclooxygenase-1 by 2-acetoxyphenylhex-2-ynyl sulfide (88).
Figure 14:
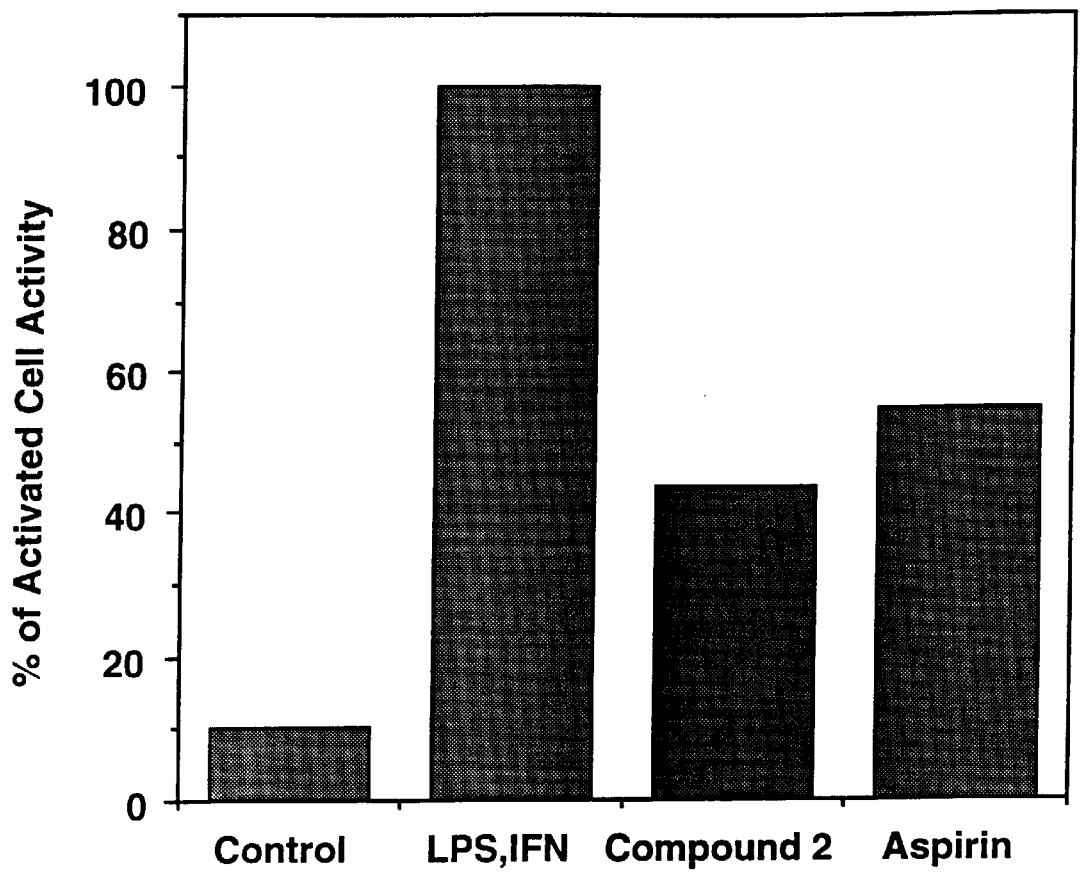
FIG. 14 shows the inhibition of cyclooxygenase-2 in activated macrophages by 2-acetoxy-thioanisole and its comparison to aspirin.
Figure 15:
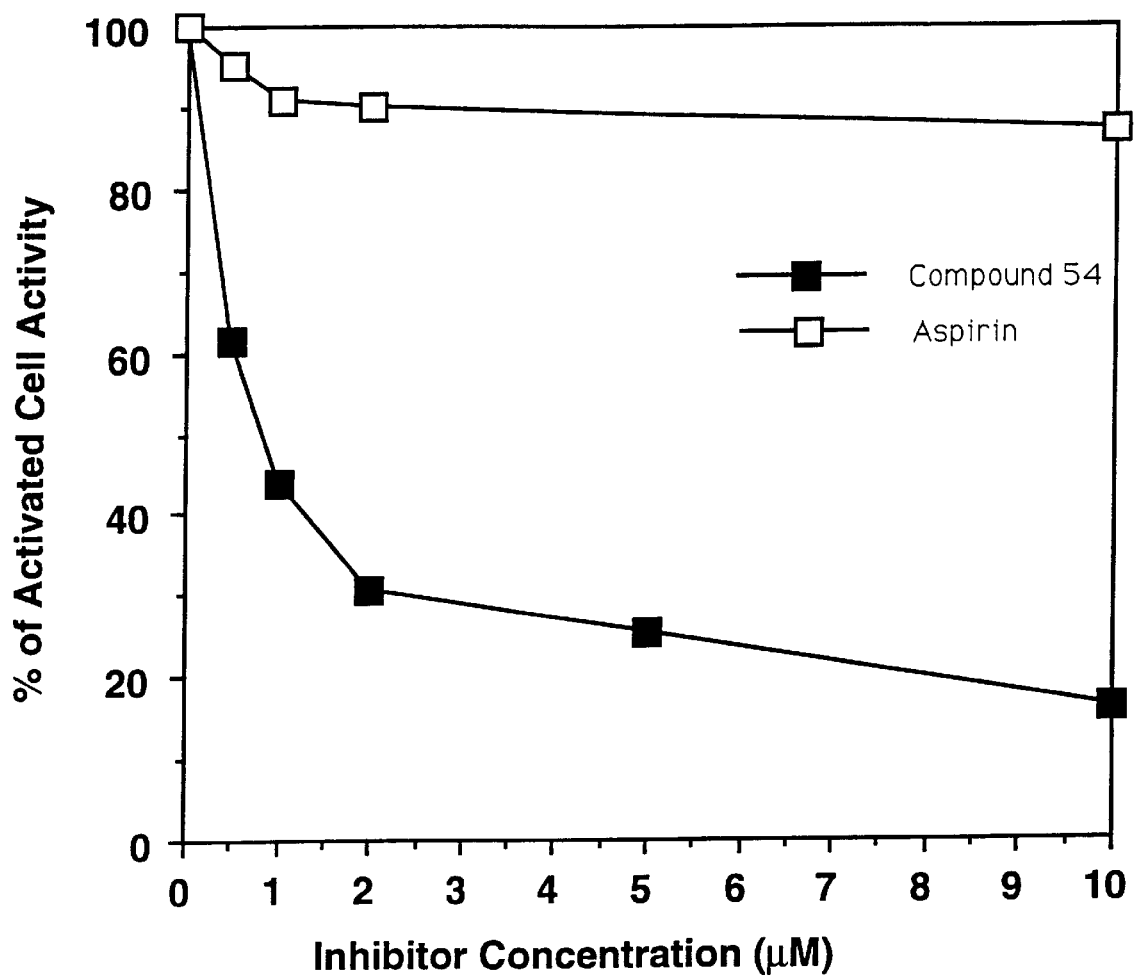
FIG. 15 shows the inhibition of PGHS-2 in activated macrophages by 2-(Acetoxyphenyl)heptyl sulfide (54) compared with aspirin.
Figure 16:
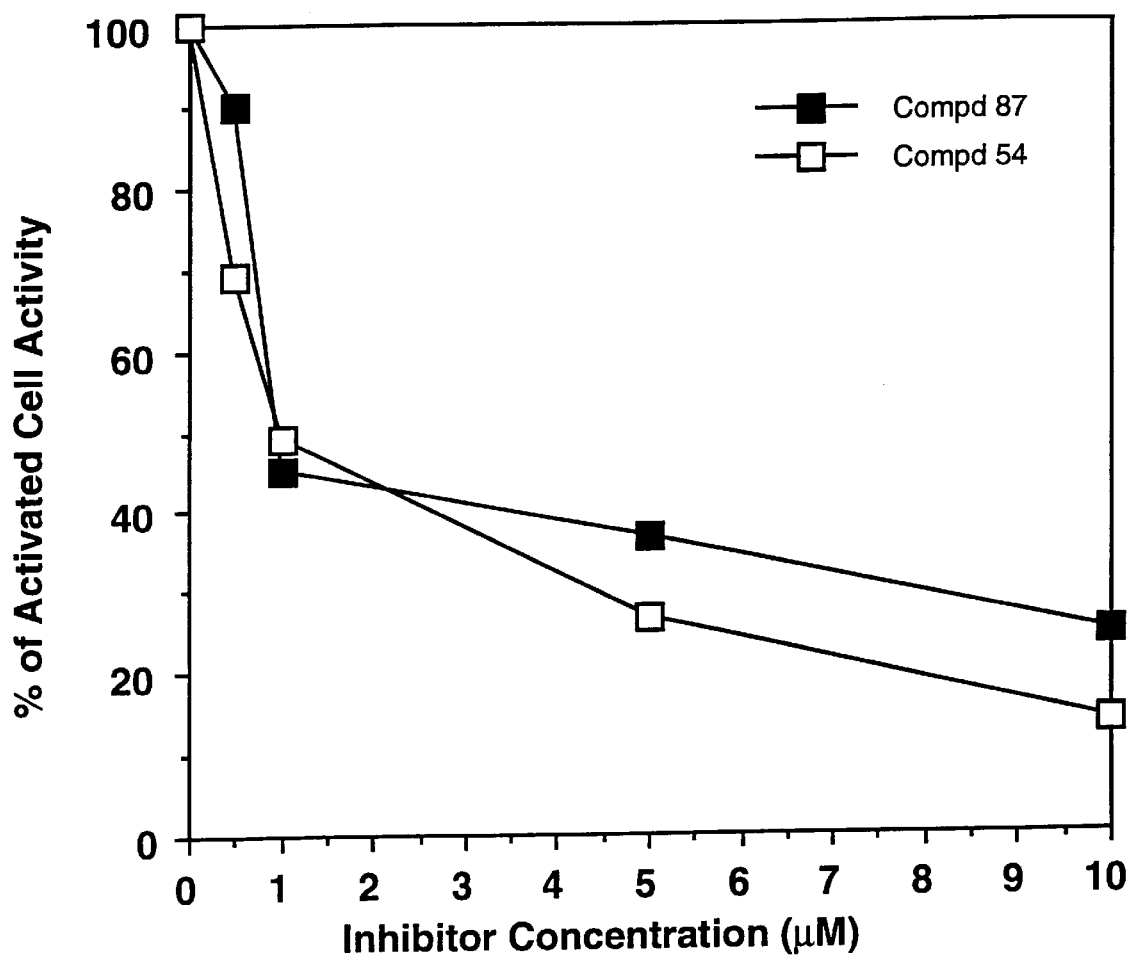
FIG. 16 shows the inhibition of PGHS-2 in activated macrophages by 2-(Acetoxyphenyl) hept-2-ynyl Sulfide (87) and 2-(Acetoxyphenyl)heptyl Sulfide (54).

FIG. 9 shows that compound 54 greatly inhibited cyclooxygenase activity of human holoPGHS-2 whereas compound 38 had very little effect. FIG. 10 shows the pH dependency of the effect of compound 54 on cyclooxygenase activity of human holoPGHS-2 with the greatest inhibition seen at pH 9. FIG. 11 shows that 8 μM of compound 67 greatly inhibited cyclooxygenase activity of human holoPGHS-2 where as compound 71 had very little effect. FIG. 12 shows that 1–16 μM compound 87 greatly inhibited cyclooxygenase activity of human holoPGHS-2 where as compound 82 had very little effect. FIG. 13 shows that 1–16 μM compound 88 greatly inhibited cyclooxygenase activity of human holoPGHS-2. FIG. 14 shows that compound 2 had a greater inhibitory effect on PGHS-2 in activated macrophages than aspirin. FIG. 15 shows that compounds 54 and 87 both greatly inhibited cyclooxygenase activity of human holoPGHS-2 in activated macrophages.

TABLE 1 shows the time and concentration-dependent inhibition of PGHS-2 and PGHS-1 by 2-acyloxyphenylalkyl and aryl sulfides, including compounds 6, 7, 8, 59, 60, 61, 62, 63 and 93. TABLE 2 shows the time and concentration-dependent inhibition of PGHS-2 and PGHS-1 by 2-acyloxyphenylalkyl and aryl sulfides, including compounds 2, 49, 50, 51, 52, 53, 54, 55, 56, 57, 58, 67, 71, 75, 87, 90 and 91.

TABLE 1

Time- and Concentration-Dependent Inhibition of PGHS-2 and PGHS-1 by 2-Acyloxyphenylalkyl and aryl Sulfides

| Cmpd | R | R' | IC50, μM (PGHS-2)[a] | IC50, μM (PGHS-1) |
|---|---|---|---|---|
| 6 | $CH_3$ | $CF_3$ | 260 | 260 |
| 7 | $CH_3$ | $CH_2Cl$ | 360 | 390 |
| 8 | $CH_3$ | $CH_2Br$ | 510 | 320 |
| 59 | $CH_2Ph$ | $CH_3$ | 250 | >400[b] |
| 60 | $(CH_2)_2Ph$ | $CH_3$ | 100 | >150[b] |
| 61 | $(CH_2)_3Ph$ | $CH_3$ | —[c] | —[c] |
| 62 | $(CH_2)_3OPh$ | $CH_3$ | —[c] | —[c] |
| 63 | $(CH_2)_7COOH$ | $CH_3$ | —[c] | >1 mM[d] |
| 93 | — | — | —[c] | —[c] |

[a]Incubations of inhibitors with PGHS-2 (88 nM) or PGHS-1 (22 nM) were conducted at room temperature for 3 hours. The cyclooygenase reaction was initiated by the addition of $^{14}$C-arachidonic acid (50 μM) to the incubation mixtures at 37° C. for 30 sec.
[b]~25–30% inhibition of PGHS-1 at these concentrations.
[c]No significant inhibition discernible at the concentrations ranges studied (66 μM to 1 mM).
*~30% inhibition of PGHS-1 at 1 mM. The fluoroacetoxythioanisole analogs 24 and 31 as well as the aspirin analog 19 did not display significant inhibition of either isozyme. Increments in the length of the acyl group (compounds 9–14) led to inactive compounds.

TABLE 2

Time- and Concentration Dependent Inhibition of PGHS-2 and PGHS-1 by 2-Acetoxyphenylalkyl and aryl Sulfides.

| Cmpnd | R | IC50, μM (PGHS-2)[a] | IC50, μM (PGHS-1) | IC50 (PGHS-1)/ IC50 (PGHS-2) |
|---|---|---|---|---|
| 2 | $CH_3$ | 250 | >5 mM | >100 |
| 49 | $CH_2CH_3$ | 20 | 375 | 1.8 |
| 50 | $(CH_2)_2CH_3$ | 66 | 66 | 1.0 |
| 51 | $(CH_2)_3CH_3$ | 40 | 34 | 1.2 |
| 52 | $(CH_2)_4CH_3$ | 5 | 5 | 1.0 |
| 53 | $(CH_2)_5CH_3$ | 3.5 | 8 | 2.3 |
| 54 | $(CH_2)_6CH_3$ | 2* | 6 | 3 |
| 55 | $(CH_2)_7CH_3$ | —[b] | —[b] | — |
| 56 | $(CH_2)_3CH_3$ | —[b] | —[b] | — |
| 57 | cyclohexyl | —[b] | —[b,c] | — |
| 58 | cycloheptyl | —[b] | —[b] | — |
| 67 | $(CH_2)_2O(CH_2)_3CH_3$ | 7 | 22 | 3 |
| 71 | $(CH_2)_3O(CH_2)_2CH_3$ | —[b] | —[b] | — |
| 75 | $CH_2CH=CH(CH_2)_3CH_3$ | 11 | —[d] | |
| 87 | $CH_2CH=C(CH_2)_3CH_3$ | 0.8 | >17 | 21 |
| 90 | $CH_2C\equiv CCH_3$ | 20 | >35 | >2 |
| 91 | $CH_2C\equiv CH$ | 25 | 40 | 1.6 |

[a]Incubations of inhibitors with PGHS-2 (88 nM) or PGHS-1 (22 nM) were conducted at room temperature for 3 hours. The cyclooygenase reaction was initiated by the addition of $^{14}$C-arachidonic acid (50 μM) to the incubation mixtures at 37° C. for 30 sec.
[b]No significant inhibition discernible at the concentration ranges (1 μM to 33 μM) studied.
[c]~14–30% inhibition of PGHS-1 at these concentrations.
*The corresponding phenol 38 did not inhibit PGHS-1 or PGHS-2; the sulfone 81 was a very poor inhibitor of either isozyme and did not display any selectivity.
[d]~25% inhibition of PGHS-1 by 75 at 16.5 μM.

TABLE 3

Time and Concentration-Dependent Inhibition of PGHS-2 and PGHS-1 by 2-acetoxyphenylalkyl and aryl sulfides

| Compound | R | R' | $IC_{50}$, μM PGHS-2[a] | $IC_{50}$, μM PGHS-1 |
|---|---|---|---|---|
| 6 | $CH_3$ | $CF_3$ | 260 | 260 |
| 7 | $CH_3$ | $CH_2Cl$ | 360 | 390 |
| 8 | $CH_3$ | $CH_2Br$ | 510 | 320 |

TABLE 3-continued

Time and Concentration-Dependent Inhibition of PGHS-2 and PGHS-1 by 2-acetoxyphenylalkyl and aryl sulfides

| Compound | R | R' | $IC_{50}$, μM PGHS-2[a] | $IC_{50}$, μM PGHS-1 |
|---|---|---|---|---|
| 59 | $CH_2Ph$ | $CH_3$ | 250 | >400[b] |
| 60 | $(CH_2)_2Ph$ | $CH_3$ | 100 | >150[b] |
| 61 | $(CH_2)_3Ph$ | $CH_3$ | —[c] | —[c] |
| 62 | $(CH_2)_3OPh$ | $CH_3$ | —[c] | —[c] |
| 63 | $(CH_2)_7COOH$ | $CH_3$ | —[c] | >1 mM[d] |
| 97 | — | — | —[c] | —[c] |

[a]Incubations of inhibitors with PGHS-2 (88 nM) or PGHS-2 (22 nM) were conducted at room temperature for 3 hours. The cyclooxygenase reaction was initiated by the addition of 14C-arachidonic acid (50 uM) to the incubation mixtures at 37 C. for 30 seconds.
[b]–25–30% inhibition of PGHS-1 at these concentrations.
[c]No significant inhibition discernible at the concentration ranges studies (66 uM to 1 mM).
*~30% inhibition of PGHS-1 at 1 mM. The fluoroacetoxythioanisole analogs 24 and 31 as well as the aspirin analog 19 did not display significant inhibition of either isozyme.

Increments in the length of the acyl group (compounds 9–14) led to inactive compounds.

The following references were cited herein:

(1) Hla, T., Neilson, K. Human Cyclooxygenase-2 cDNA. *Proc. Natl. Acad. Sci. U.S.A.* 1992, 89, 7384–7388.

(2) Xie, W., Chipman, J. G., Robertson, D. L., Erickson, R. L., Simmons, D. L. Expression of a Mitogen-Response Gene Encoding Prostaglandin Synthase is Regulated mRNA splicing. *Proc. Natl. Acad. Sci. U.S.A.* 1991, 88, 2692–2696.

(3) Kujubu, D. A., Fletcher, B. S., Varnum, B. C., Lim, R. W., Herschman, H. R. TIS10, a Phorbol Ester Tumor Promoter-Inducible mRNA From Swiss 3T3 Cells, Encodes a Novel Prostaglandin Synthase/Cyclooxygenase Homologue. *J. Biol. Chem.* 1991, 266, 12866–12872.

(4) Masferrer, J. L., Seibert, K., Zweifel, B., Needleman, P. Endogenous Glucocorticoids Regulate an Inducible Cyclooxygenase Enzyme. *Proc. Natl. Acad. Sci. U.S.A.* 1992, 89, 3917–3921.

(5) Allison, M. C., Howatson, A. G., Torrance, C. J., Lee, F. D., Russell, R. I. G. Gastrointestinal Damage Associated With the Use of Nonsteroidal Antiinflammatory Drugs. *N. Engl. J. Med.* 1992, 327, 749–754.

(6) Clive, D. M., Stoff, J. S. Renal Syndromes Associated With Nonsteroidal Antiinflammatory Drugs. *N. Engl. J. Med.* 1984, 310, 563–572.

(7) Pirson, Y., Van Ypersele de Strihou, C. Renal Side Effects of Nonsteroidal Antiinflammatory Drugs: Clinical Relevance. *Am. J. Kidney Dis.* 1986, 8, 337–344.

(8) Futaki, N., Yoshikawa, K., Hamasaka, Y., Arai, I., Higuchi, S., Iizuka, H., Otomo, S. NS-398, A Novel Nonsteroidal Antiinflammatory Drug With Potent Analgesic and Antipyretic Effects, Which Causes Minimal Stomach Lesions. *Gen. Pharmacol.* 1993, 24, 105–110.

(9) Futaki, N., Takahashi, S., Yokoyama, M., Arai, I., Higuchi, S., Otomo, S. NS-398, A New Anti-Inflammatory Agent, Selectively Inhibits Prostaglandin G/H Synthase/Cyclooxygenase (COX-2) Activity In Vitro. *Prostaglandins* 1994, 47, 55–59.

(10) Li, C -S., Black, W. C., Chan, C -C., Ford-Hutchinson, A. W., Gauthier, J -Y., Gordon, R., Guay, D., Kargman, S., Lau, C. K., Mancini, J., Quimet, N., Roy, P., Vickers, P., Wong, E., Young, R. N., Zamboni, R., Prasit, P. Cyclooxygenase-2 Inhibitors. Synthesis and Pharmacological Activities of 5-Methanesulfonamido-1-indanone Derivatives. *J. Med. Chem.* 1995, 38, 4897–4905.

(11) Huff, R., Collins, P., Kramer, S., Seibert, K., Koboldt, C., Gregory, S., Isakson, P. A Structural Feature of N-[2-(Cyclohexyloxy)-4-nitrophenyl] methanesulfonamide (NS-398) That Governs its Selectivity and Affinity for Cyclooxygenase 2 (COX2). *Inflamm. Res.* 1995, 44:Suppl. 2, S145–S146.

(12) Gan, K. R., Galbraith, W., Roman, R. J., Haber, S. B., Kerr, J. S., Schmidt, W. K., Smith, C., Hewes, W. E., Ackerman, N. R. Anti-Inflammatory and Safety Profile of DuP 697, a Novel Orally Effective Prostaglandin Synthesis Inhibitor. *J. Pharmacol. Exp. Ther.* 1990, 254, 180–187.

(13) Seibert, K., Zhang, Y., Leahy, K., Hauser, S., Masferrer, P., William, L. L., Isakson, P. C. Pharmacological and Biochemical Demonstration of the Role of Cyclooxygenase-2 in Inflammation. *Proc. Natl. Acad. Sci. U.S.A.* 1994, 91, 12013–12017.

(14) Kalgutkar, A. S., Crews, B. C., Marnett, L. J. Kinetics of the Interaction of Nonsteroidal Anti-inflammatory Drugs With Prostaglandin Endoperoxide Synthase-1 Studied by Limited Proteolysis. *Biochemistry* 1996, 35, 9076–9082.

(15) Li, J. J., Norton, M. B., Reinhard, E. J., Anderson, G. D., Gregory, S. A., Isakson, P. C., Koboldt, C. M., Masferrer, J. L., Perkins, W. E., Seibert, K., Zhang, Y., Zweifel, B. S., Reitz, D. B. Novel Terphenyls as Selective Cyclooxygenase-2 Inhibitors and Orally Active Anti-Inflammatory Agents. *J. Med. Chem.* 1996, 39, 1846–1856.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound of the formula wherein R is selected from the group consisting of $CH_3$, $CH_2CH_3$, $CH_2Ph$, $(CH_2)_2Ph$, $(CH_2)_2CH_3$, $(CH_2)_3CH_3$, $(CH_2)_4CH_3$, $(CH_2)_5CH_3$, $(CH_2)_6CH_3$, $(CH_2)_2O(CH_2)_3CH_3$, $CH_2HC=CH(CH_2)_3CH_3$, $CH_2C\equiv C(CH_2)_3CH_3$, $CH_2C\equiv C(CH_2)_2CH_3$, $CH_2C\equiv CCH_2CH_3$, $CH_2C\equiv CCH_3$, and $CH_2C\equiv CH$;

wherein R' is selected from the group consisting of $CH_3$, $CF_3$, $CH_2Cl$, and $CH_2Br$;

wherein when R is $CH_3$, R' can not be $CH_3$ or $CH_2Cl$;

wherein when R is $CH_2CH_3$, R' can not be $CH_3$; or pharmaceutically acceptable salts or hydrates thereof.

2. The compound of claim 1 which is 2-(trifluoromethylacetoxy)thioanisole, or a pharmaceutically acceptable salt or hydrate thereof.

3. The compound of claim 1 which is 2-($\alpha$-bromoacetoxy)thioanisole, or a pharmaceutically acceptable salt or hydrate thereof.

4. The compound of claim 1 which is 2-acetoxyphenylbenzyl sulfide, or a pharmaceutically acceptable salt or hydrate thereof.

5. The compound of claim 1 which is 2-acetoxyphenyl-2-phenylethyl sulfide, or a pharmaceutically acceptable salt or hydrate thereof.

6. The compound of claim 1, which is 2-acetoxyphenylpropyl sulfide, or a pharmaceutically acceptable salt or hydrate thereof.

7. The compound of claim 1, which is 2-acetoxyphenylbutyl sulfide, or a pharmaceutically acceptable salt or hydrate thereof.

8. The compound of claim 1, which is 2-acetoxyphenylpentyl sulfide, or a pharmaceutically acceptable salt or hydrate thereof.

9. The compound of claim 1, which is 2-acetoxyphenylhexyl sulfide, or a pharmaceutically acceptable salt or hydrate thereof.

10. The compound of claim 1, which is 2-acetoxyphenylheptyl sulfide, or a pharmaceutically acceptable salt or hydrate thereof.

11. The compound of claim 1, which is 2-acetoxyphenyl-2-butoxyethyl sulfide, or a pharmaceutically acceptable salt or hydrate thereof.

12. The compound of claim 1, which is 2-Acetoxyphenyl-2-trans-heptenyl sulfide, or a pharmaceutically acceptable salt or hydrate thereof.

13. The compound of claim 1, which is 2-acetoxyphenylhept-2-ynyl sulfide, or a pharmaceutically acceptable salt or hydrate thereof.

14. The compound of claim 1, which is 2-acetoxyphenylhex-2-ynyl sulfide, or a pharmaceutically acceptable salt or hydrate thereof.

15. The compound of claim 1, which is 2-acetoxyphenylpent-2-ynyl sulfide, or a pharmaceutically acceptable salt or hydrate thereof.

16. The compound of claim 1, which is 2-acetoxyphenylbut-2-ynyl sulfide, or a pharmaceutically acceptable salt or hydrate thereof.

17. The compound of claim 1, which is 2-acetoxyphenylprop-2-ynyl sulfide, or a pharmaceutically acceptable salt or hydrate thereof.

18. A method of inhibiting the synthesis of prostaglandin endoperoxide synthase-2 (PGHS-2) in a mammal in need of such treatment, comprising the step of administering to said mammal an effective amount of a compound of Formula (I) of claim 1.

19. The method of claim 18, wherein inhibition of prostaglandin endoperoxide synthase-2 is useful in the prophylaxis or therapeutic treatment of edema, fever, algesia, neuromuscular pain, headache, cancer pain or arthritic pain.

20. The method of claim 8, wherein said compound is selected from the group consisting of 2-acetoxythioanisole, 2-(trifluoromethylacetoxy)thioanisole, 2-($\alpha$-chloroacetoxy)thioanisole, 2-($\alpha$-bromoacetoxy)thioanisole, 2-acetoxyphenylbenzyl sulfide, 2-acetoxyphenyl-2-phenylethyl sulfide, 2-acetoxyphenylethyl sulfide, 2-acetoxyphenylpropyl sulfide, 2-acetoxyphenylbutyl sulfide, 2-acetoxyphenylpentyl sulfide, 2-acetoxyphenylhexyl sulfide, 2-acetoxyphenylheptyl sulfide, 2-acetoxyphenyl-2-butoxyethyl sulfide, 2-acetoxyphenyl-2-trans-heptenyl sulfide, 2-acetoxyphenylhept-2-ynyl sulfide, 2-acetoxyphenylhex-2-ynyl sulfide, 2-acetoxyphenylpent-2-ynyl sulfide, 2-acetoxyphenylbut-2-ynyl sulfide and 2-acetoxyphenylprop-2-ynyl sulfide, or pharmaceutically acceptable salts or hydrates thereof.

21. A pharmaceutical composition, comprising a compound of Formula (I) of claim 1 and a pharmaceutically acceptable carrier or diluent.

22. The pharmaceutical composition of claim 21, wherein said compound is selected from the group consisting of 2-(trifluoromethylacetoxy)thioanisole, 2-($\alpha$-bromoacetoxy)thioanisole, 2-acetoxyphenylbenzyl sulfide, 2-acetoxyphenyl-2-phenylethyl sulfide, 2-acetoxyphenylpropyl sulfide, 2-acetoxyphenylbutyl sulfide, 2-acetoxyphenylpentyl sulfide, 2-acetoxyphenylhexyl sulfide, 2-acetoxyphenylheptyl sulfide, 2-acetoxyphenyl-2-butoxyethyl sulfide, 2-acetoxyphenyl-2-trans-heptenyl sulfide, 2-acetoxyphenylhept-2-ynyl sulfide, 2-acetoxyphenylhex-2-ynyl sulfide, 2-acetoxyphenylpent-2-ynyl sulfide, 2-acetoxyphenylbut-2-ynyl sulfide and 2-acetoxyphenylprop-2-ynyl sulfide, or pharmaceutically acceptable salts or hydrates thereof.

* * * * *